United States Patent
North et al.

(10) Patent No.: US 11,872,227 B2
(45) Date of Patent: Jan. 16, 2024

(54) PHARMACEUTICAL COMBINATIONS COMPRISING A HISTONE DEACETYLASE INHIBITOR AND AN AURORA KINASE INHIBITOR AND METHODS OF USE THEREOF

(71) Applicant: ACETYLON PHARMACEUTICALS, INC., Boston, MA (US)

(72) Inventors: Brian North, Boston, MA (US); Steven Quayle, Brookline, MA (US)

(73) Assignee: ACETYLON PHARMACEUTICALS, INC., Boston, MA (US)

( * ) Notice: Subject to any disclaimer, the term of this patent is extended or adjusted under 35 U.S.C. 154(b) by 58 days.

(21) Appl. No.: 17/741,146

(22) Filed: May 10, 2022

(65) Prior Publication Data

US 2022/0362243 A1 Nov. 17, 2022

Related U.S. Application Data

(62) Division of application No. 16/344,886, filed as application No. PCT/US2017/058794 on Oct. 27, 2017, now Pat. No. 11,357,776.

(60) Provisional application No. 62/414,468, filed on Oct. 28, 2016.

(51) Int. Cl.
*A61K 31/505* (2006.01)
*A61P 35/00* (2006.01)
*A61K 31/55* (2006.01)

(52) U.S. Cl.
CPC ............ *A61K 31/505* (2013.01); *A61K 31/55* (2013.01); *A61P 35/00* (2018.01)

(58) Field of Classification Search
CPC .................................................. A61K 31/505
See application file for complete search history.

(56) References Cited

U.S. PATENT DOCUMENTS

| | | | |
|---|---|---|---|
| 2015/0072988 A1 | 3/2015 | Carducci et al. | |
| 2015/0105409 A1 | 4/2015 | Quayle et al. | |

FOREIGN PATENT DOCUMENTS

| | | |
|---|---|---|
| WO | WO 2011/091213 | 7/2011 |
| WO | WO 2015/054197 A1 | 4/2015 |
| WO | WO 2015/085789 A1 | 6/2015 |
| WO | WO2015173544 A1 | 11/2015 |
| WO | WO2016106357 A1 | 6/2016 |

OTHER PUBLICATIONS

U.S. Appl. No. 13/010,974 / 2011/0300134 / U.S. Pat. No. 8,394,810, filed Jan. 21, 2011 / Dec. 8, 2011 / Mar. 12, 2013, John H. van Duzer.
U.S. Appl. No. 13/310,168 / 2012/0083504 / U.S. Pat. No. 8,148,526, filed Dec. 2, 2011 / Apr. 5, 2012 / Apr. 3, 2012, John H. van Duzer.
U.S. Appl. No. 13/437,672 / 2012/0190693/ U.S. Pat. No. 8,609,678, filed Apr. 2, 2012 / Jul. 26, 2012 / Dec. 17, 2013, John H. van Duzer.
U.S. Appl. No. 13/296,748 / 2012/0121502 / U.S. Pat. No. 8,614,223, filed Dec. 24, 2013 / May 17, 2012 / Dec. 24, 2013, John H. Van Duzer.
U.S. Appl. No. 14/082,472 / 2014/0142104/ U.S. Pat. No. 9,409,890, filed Nov. 18, 2013 / May 22, 2014 / Aug. 9, 2017, John H. van Duzer.
U.S. Appl. No. 13/866,367 / 2014/0011767 / U.S. Pat. No. 9,663,825, filed Apr. 19, 2013 / 2014/0011767 / May 30, 2017, Min Yang.
U.S. Appl. No. 15/497,397 / 2017/0327895 / U.S. Pat. No. 10,648,038, filed Apr. 26, 2017 / Nov. 16, 2017 / May 12, 2020, Min Yang.
U.S. Appl. No. 14/508,072 / 2015/0105358, filed Oct. 7, 2014 / Apr. 16, 2015, Steven Norman Quayle.
U.S. Appl. No. 14/506,889 / 2015/0099744 / U.S. Pat. No. 9,403,779, filed Oct. 6, 2014 / Apr. 9, 2015 / Aug. 2, 2016, David Lee Tamang.
U.S. Appl. No. 15/189,554 / 2017/0020872 / U.S. Pat. No. 10,722,512, filed Jun. 22, 2016 / Jan. 26, 2017 / Jul. 28, 2020, David Lee Tamang.
U.S. Appl. No. 14/508,135 / 2015/0105409, filed Oct. 7, 2014 / Apr. 16, 2015, Steven Norman Quayle.
U.S. Appl. No. 14/509,360 / 2015/0105383, filed Oct. 8, 2014 / Apr. 16, 2015, Steven Norman Quayle.
U.S. Appl. No. 14/510,711 / 2015/0105384 / U.S. Pat. No. 9,278,963, filed Oct. 9, 2014 / Apr. 16, 2015 / Mar. 8, 2016, John H. van Duzer.
U.S. Appl. No. 14/631,971 / 2015/0239869 / U.S. Pat. No. 9,464,073, filed Feb. 26, 2015 / Aug. 27, 2015 / Oct. 11, 2016, Ralph Mazitschek.
U.S. Appl. No. 15/260,855 / 2017/0096413 / U.S. Pat. No. 9,884,850, filed Sep. 9, 2016 / Apr. 6, 2017 / Feb. 6, 2018, Ralph Mazitschek.
U.S. Appl. No. 14/558,941 / 2015/0150871 / U.S. Pat. No. 9,949,972, filed Dec. 3, 2014 / Jun. 4, 2015 / Apr. 24, 2018, Steven Norman Quayle.
U.S. Appl. No. 14/576,313 / 2015/0176076, filed Dec. 19, 2014 / Jun. 25, 2015, Min Yang.
U.S. Appl. No. 14/792,046 / 2016/0030458 / U.S. Pat. No. 9,833,466, filed Jul. 6, 2015 / Feb. 4, 2016 / Dec. 5, 2017, Simon S. Jones.
U.S. Appl. No. 14/959,473 / 2016/0158232 / U.S. Pat. No. 9,937,174, filed Dec. 4, 2015 / Jun. 9, 2016 / Apr. 10, 2018, Samantha Pozzi.
U.S. Appl. No. 15/176,826 / 2016/0355486 / U.S. Pat. No. 10,144,714, filed Jun. 8, 2016 / Dec. 8, 2016 / Dec. 4, 2018, Farzaneh Seyedi.
U.S. Appl. No. 15/176,788 / 2017/0001965 / U.S. Pat. No. 10,464,906, filed Jun. 8, 2016 / Jan. 5, 2017 / Nov. 5, 2019, John H. van Duzer.
U.S. Appl. No. 16/076,590 / 2019/0046529 / U.S. Pat. No. 11,311,540, filed Feb. 17, 2017 / Feb. 14, 2019 / Apr. 26, 2022, Steven Norman Quayle.

(Continued)

*Primary Examiner* — Yong S. Chong
(74) *Attorney, Agent, or Firm* — Brian C. Trinque; Lathrop GPM LLP

(57) ABSTRACT

The present disclosure relates to a pharmaceutical combination comprising (a) a histone deacetylase 6 inhibitor and (b) an aurora kinase inhibitor, including combined preparations and pharmaceutical compositions thereof; uses of such combination in the treatment or prevention of cancer; and methods of treating or preventing cancer in a subject comprising administering a therapeutically effective amount of such combination.

4 Claims, 7 Drawing Sheets

(56) References Cited

OTHER PUBLICATIONS

U.S. Appl. No. 17/701,222, filed Mar. 22, 2022, Steven Norman Quayle.
U.S. Appl. No. 16/093,278 / 2019/0209559/, filed Apr. 19, 2017 / Jul. 11, 2019, Simon S. Jones.
U.S. Appl. No. 15/670,743 / 2018/0036306 / U.S. Pat. No. 11,324,744, filed Aug. 7, 2017 / Feb. 8, 2018 / May 10, 2022, Simon Steward Jones.
U.S. Appl. No. 16/305,567, filed Jun. 9, 2017, Kwok-kin Wong.
U.S. Appl. No. 16/344,453 / 2019/0321361, filed Apr. 24, 2019 / Oct. 24, 2019, Pengyu Huang.
U.S. Appl. No. 16/377,873 / 2019/0262337, filed Nov. 3, 2017 / Aug. 29, 2019, Nathan Moore.
U.S. Appl. No. 15/807,782 / 2018/0127356 / U.S. Pat. No. 10,370,324, filed Nov. 9, 2017 / May 10, 2018 / Aug. 6, 2019, John H. van Duzer.
U.S. Appl. No. 16/344,886 / 2020/0046698 /, filed Apr. 25, 2022 / Feb. 13, 2020 /, Brian North.
International Search Report and Written Opinion corresponding to International Patent Application No. PCT/US2017/058794, dated Jan. 4, 2018 (12 pages).
Choudary et al., "Recent advances in the development of Aurora kinases inhibitors in hematological malignancies", Therapeutic Advances in hematology, 2015, vol. 6(6) 282-294, doi: 10.11777/2040620715607415.
Gavriilidis et al., "Aurora Kinases and Potential Medical Applications of Aurora Kinase Inhibitors: A Review", J. clin. Med. Res. 2015,(10): 742-751, doi: http://dx.doi.org/10.14740/jocmr2295w.

Melichar et al., "Safety and activity of alisertib, an investigational aurora kinase A inhibitor, in patients with breast cancer, small-call lung cancer, non-small-ell lung cancer, head and neck squamous-cell carcinoma, and gastro-oesophageal adenocarcinoma: a five-arm phase 2 study", The Lancet Oncology, 2015, 16: 395-405.
Jennifer E Amengual et al: "Translational Focus on Targeting HDAC6 with Ricolinostat Confirms Potent Activity in Preclinical Models of Lymphoma and a Favorable Toxicity Profile in Patients with Relapsed or Refractory Lymphoma I Blood I American Society of Hematology", Blood, Dec. 2015, Retrieved from the Internet: URL:https://ashpublications.org/blood/article/126/23/1280/104833/Translational-Focus-on-Targeting-HDAC6-with.
K. M. Zullo et al: "Aurora A Kinase Inhibition Selectively Synergizes with Histone Deacetylase Inhibitor through Cytokinesis Failure in T-cell Lymphoma", Clinical Cancer Research, vol. 21, No. 18, Apr. 15, 2015, pp. 4097-4109.
Seiichi Okabe et al: "Activity of histone deacetylase inhibitors and an Aurora kinase inhibitor in BCR-ABL-expressing leukemia cells: Combination of HDAC and Aurora inhibitors in BCR-ABL-expressing cells", Cancer Cell International, vol. 13, No. 1, Apr. 4, 2013, p. 32.
Dan T Vogl et al: "Phase 1B Results of Ricolinostat (ACY-1215) Combination Therapy with Bortezomib and Dexamethasone in Patients with Relapsed or Relapsed and Refractory Multiple Myeloma (MM) I Blood I American Society of Hematology", Blood, Dec. 2014.
Loredana Santo et al: "Preclinical activity, pharmacodynamic, and pharmacokinetic properties of a selective HDAC6 inhibitor, ACY-1215, in combination with bortezomib in multiple myeloma", Blood, vol. 119, No. 11,Mar. 15, 2012, pp. 2579-2589.
Varga C et al: "Novel Targeted Agents in the Treatment of Multiple Myeloma", Hematology—Oncology Clinics of North America, vol. 28, No. 5, Oct. 1, 2014, pp. 903-925.

PHARMACEUTICAL COMBINATIONS COMPRISING A HISTONE DEACETYLASE INHIBITOR AND AN AURORA KINASE INHIBITOR AND METHODS OF USE THEREOF

CROSS-REFERENCE TO RELATED APPLICATIONS

This application claims the benefit of U.S. Provisional Application No. 62/414,468, filed Oct. 28, 2016, the contents of which are incorporated herein by reference in their entirety.

BACKGROUND

Histone deacetylase (HDAC) inhibition can cause cancer cell growth arrest. However, pan-HDAC inhibition leads to significant adverse effects and an alternative HDAC inhibition profile is desirable.

HDAC6 is a Class IIb HDAC and is known to remove acetyl groups from many cellular proteins, including α-tubulin and HSP90. It has been reported that HSP90 hyperacetylation destabilizes its target proteins, including ER and EGFR. Inhibitors of HDAC6 have demonstrated anti-cancer proliferative activity in various cancer types. Blocking HDAC6 activity has been shown to cause cancer cell growth inhibition through various mechanisms.

In spite of numerous treatment options for cancer patients, there remains a need for effective and safe therapeutic options. In particular, there is a need for effective methods of treating or preventing cancers, especially those cancers that have been resistant and/or refractive to current therapies. This need can be fulfilled by the use of combination therapies such as those described herein.

SUMMARY

Provided herein is a pharmaceutical combination comprising a histone deacetylase (HDAC) inhibitor and an aurora kinase inhibitor.

In an aspect, provided herein is a pharmaceutical combination comprising:
(a) a histone deacetylase 6 (HDAC6) inhibitor of Formula I:

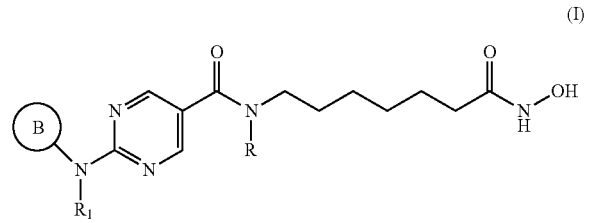

or a pharmaceutically acceptable salt thereof,
wherein,
ring B is aryl or heteroaryl;
$R_1$ is aryl or heteroaryl, each of which may be optionally substituted by OH, halo, or $C_{1-6}$-alkyl;
and
R is H or $C_{1-6}$-alkyl; and
(b) an aurora kinase inhibitor.
In various embodiments of the pharmaceutical combination, ring B is aryl.

In various embodiments of the pharmaceutical combination, $R_1$ is aryl or heteroaryl, each of which may be optionally substituted by halo.

In an embodiment of Formula I, $R_1$ is an aryl that is substituted by OH, halo, or $C_{1-6}$-alkyl.

In another embodiment of Formula I, $R_1$ is $C_5$-$C_7$ aryl that is substituted by OH, halo, or $C_{1-6}$-alkyl.

In another embodiment of Formula I, $R_1$ is $C_4$-$C_7$ heteroaryl that is substituted by OH, halo, or $C_{1-6}$-alkyl.

In yet another embodiment of Formula I, $R_1$ is phenyl that is substituted by OH, halo, or $C_{1-6}$-alkyl.

In yet another embodiment of Formula I, $R_1$ is phenyl that is substituted by chloro.

In yet another embodiment of Formula I, $R_1$ is phenyl that is substituted by halo.

In another embodiment of Formula I, ring B is $C_5$-$C_7$ aryl.

In another embodiment of Formula I, ring B is $C_4$-$C_7$ heteroaryl.

In yet another embodiment of Formula I, ring B is phenyl.

In various embodiments of the pharmaceutical combination, the HDAC6 inhibitor of Formula I is:

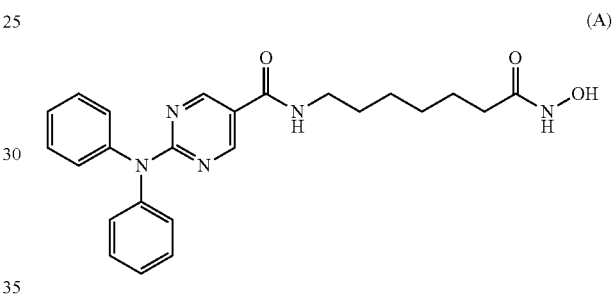

or a pharmaceutically acceptable salt thereof.

In various embodiments of the pharmaceutical combination, the HDAC6 inhibitor of Formula I is:

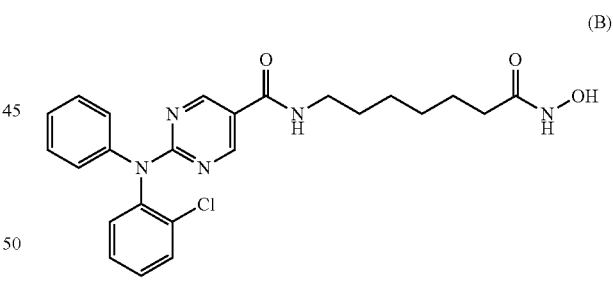

or a pharmaceutically acceptable salt thereof.

In various embodiments of the pharmaceutical combination, the aurora kinase inhibitor is selected from the group consisting of alisertib, AT-9283, barasertib, ENMD-2076, MK-5108, MSC 1992371A, danusertib, and tozasertib, or pharmaceutically acceptable salts thereof.

In various embodiments of the pharmaceutical combination, the aurora kinase inhibitor is alisertib, or a pharmaceutically acceptable salt thereof.

In various embodiments of the pharmaceutical combination, the HDAC6 inhibitor and the aurora kinase inhibitor are in the same formulation. In other embodiments of the pharmaceutical combination, the HDAC6 inhibitor and the aurora kinase inhibitor are in separate formulations.

In various embodiments of the pharmaceutical combination, the combination is for simultaneous or sequential administration.

In various embodiments, the pharmaceutical combination is for use in treating cancer in a subject in need thereof.

In other various embodiments, the pharmaceutical combination is for use in the preparation of a medicament for the treatment of cancer.

In various embodiments, the cancer is a lymphoma, leukemia, or myeloma. In particular embodiments, the cancer is non-Hodgkin's lymphoma (NHL), chronic myelogenous leukemia (CML), acute myelogenous leukemia (AML), or multiple myeloma (MM). In further embodiments, the cancer is a T-cell lymphoma or B-cell lymphoma.

In various embodiments of the pharmaceutical combination, the cancer is a solid tumor. In particular embodiments, the cancer is lung cancer (e.g., small cell lung cancer).

In an aspect, provided herein is a method for treating or preventing cancer in a subject in need thereof, comprising administering to the subject a therapeutically effective amount of a pharmaceutical combination provided herein.

In an embodiment of the method, the cancer is a lymphoma, leukemia, or myeloma. In particular embodiments of the method, the cancer is non-Hodgkin's lymphoma (NHL), chronic myelogenous leukemia (CML), acute myelogenous leukemia (AML), or multiple myeloma (MM). In further embodiments, the cancer is a T-cell lymphoma or B-cell lymphoma.

In various embodiments of the method, the cancer is a solid tumor. In particular embodiments of the method, the cancer is lung cancer (e.g., small cell lung cancer).

In various embodiments of the method, the HDAC6 inhibitor and the aurora kinase inhibitor are administered at approximately the same time. In other embodiment, the HDAC6 inhibitor and the aurora kinase inhibitor are administered at different times.

In an aspect, provided herein is a method of decreasing cell growth and viability, comprising contacting the cell with a pharmaceutical combination of any one of claims 1-10, wherein the cell is a myeloma cell or a lymphoma cell.

In an aspect, provided herein is a pharmaceutical composition comprising
(a) a histone deacetylase 6 (HDAC6) inhibitor of Formula I:

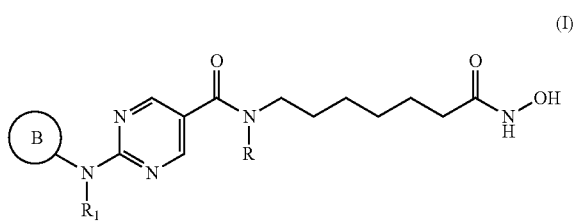

(I)

or a pharmaceutically acceptable salt thereof,
wherein,
ring B is aryl or heteroaryl;
$R_1$ is aryl or heteroaryl, each of which may be optionally substituted by OH, halo, or $C_{1-6}$-alkyl;
and
R is H or $C_{1-6}$-alkyl; and
(b) an aurora kinase inhibitor.

In an embodiment of the composition, the pharmaceutical composition further comprises one or more excipients.

In an embodiment of the composition, ring B is aryl. In various embodiments, $R^1$ is aryl or heteroaryl, each of which may be optionally substituted by halo.

In another embodiment of the composition, the compound of Formula I is:

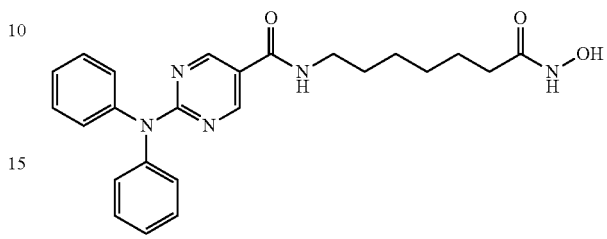

(A)

or a pharmaceutically acceptable salt thereof.

In another embodiment of the composition, the compound of Formula I is:

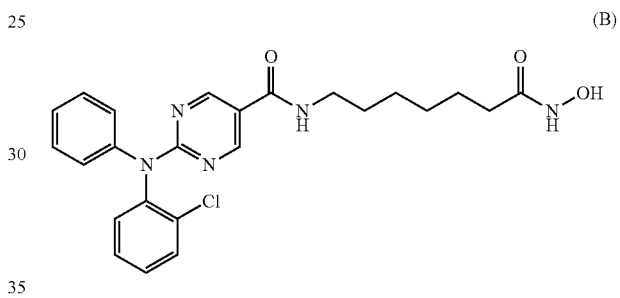

(B)

or a pharmaceutically acceptable salt thereof.

In various embodiments of pharmaceutical composition, the aurora kinase inhibitor is selected from the group consisting of alisertib, AT-9283, barasertib, ENMD-2076, MK-5108, MSC 1992371A, danusertib, and tozasertib, or pharmaceutically acceptable salts thereof. In particular embodiments, the aurora kinase inhibitor is alisertib, or a pharmaceutically acceptable salt thereof.

DETAILED DESCRIPTION

Figure 1:
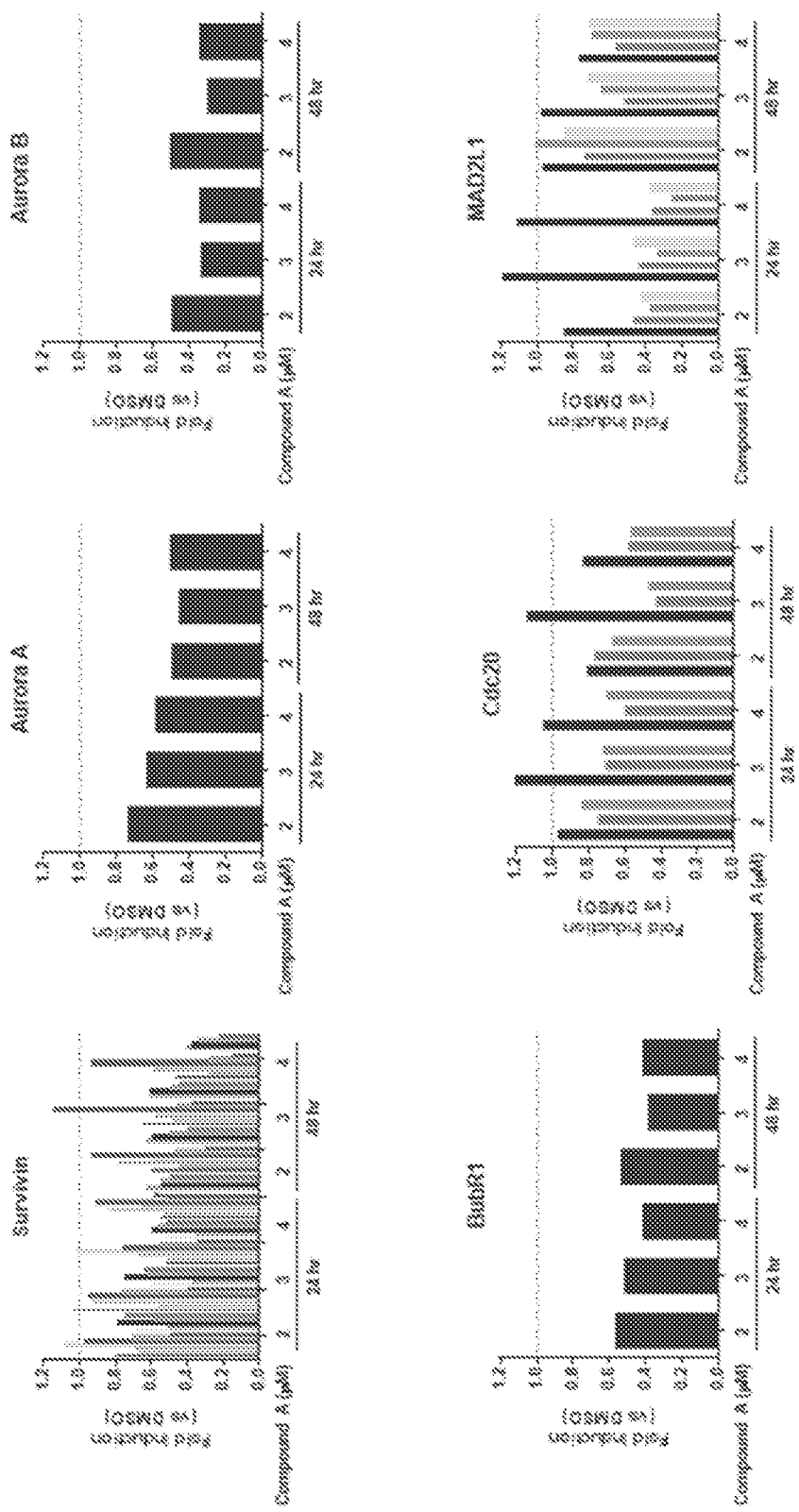
FIG. 1 is a series of bar graphs showing the relative fold induction of the indicated gene transcripts by Compound A as compared to dimethyl sulfoxide (DMSO) treatment of H929 multiple myeloma cells for 24 hours and 48 hours. The measured gene transcripts are: survivin, Aurora A, Aurora B, BubR1, CDC20 and MAD2L1.

Provided herein is a pharmaceutical combination comprising a histone deacetylase inhibitor (HDAC) inhibitor and an aurora kinase inhibitor. Specifically, provided herein is a pharmaceutical combination comprising:

(a) a histone deacetylase 6 (HDAC6) inhibitor of Formula I:

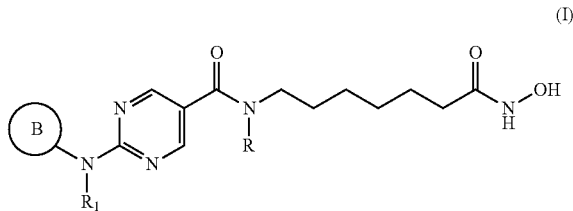

(I)

or a pharmaceutically acceptable salt thereof,
wherein,
ring B is aryl or heteroaryl;
$R_1$ is aryl or heteroaryl, each of which may be optionally substituted by OH, halo, or $C_{1-6}$-alkyl;
and
R is H or $C_{1-6}$-alkyl; and
(b) an aurora kinase inhibitor, or a pharmaceutically acceptable salt thereof.

Certain terms used herein are described below. Compounds of the present invention are described using standard nomenclature. Unless defined otherwise, all technical and scientific terms used herein have the same meaning as is commonly understood by one of skill in the art to which this invention belongs.

Definitions

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties. The number of carbon atoms in an alkyl substituent can be indicated by the prefix "$C_{x-y}$," where x is the minimum and y is the maximum number of carbon atoms in the substituent.

As used herein, the term "halo" or "halogen" alone or as part of another substituent means, unless otherwise stated, a fluorine, chlorine, bromine, or iodine atom, preferably, fluorine, chlorine, or bromine, more preferably, chlorine.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl, and the like. In some embodiments, aryl groups have 6 carbon atoms. In some embodiments, aryl groups have from six to ten carbon atoms. In some embodiments, aryl groups have from six to sixteen carbon atoms. In an embodiment, $C_5$-$C_7$ aryl groups are provided herein.

The term "heteroaryl" refers to a mono- or poly-cyclic (e.g., bi-, or tri-cyclic or more) fused or non-fused moiety or ring system having at least one aromatic ring, where one or more of the ring-forming atoms is a heteroatom such as oxygen, sulfur, or nitrogen. In some embodiments, the heteroaryl group has from about one to six carbon atoms, and in further embodiments from one to fifteen carbon atoms. In some embodiments, the heteroaryl group contains five to sixteen ring atoms of which one ring atom is selected from oxygen, sulfur, and nitrogen; zero, one, two, or three ring atoms are additional heteroatoms independently selected from oxygen, sulfur, and nitrogen; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiazolyl, thiadiazolyl, oxadiazolyl, thiophenyl, furanyl, indolyl, quinolinyl, isoquinolinyl, benzimidazolyl, benzooxazolyl, quinoxalinyl, acridinyl, and the like. In an embodiment, $C_4$-$C_7$ heteroaryl groups are provided herein.

The term "combination," "therapeutic combination," or "pharmaceutical combination" as used herein refer to either a fixed combination in one dosage unit form, or non-fixed combination, or a kit of parts for the combined administration where two or more therapeutic agents may be administered independently, at the same time or separately within time intervals, especially where these time intervals allow that the combination partners show a cooperative, e.g., synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single formulation having a fixed ratio of active ingredients or in separate formulations (e.g., capsules and/or intravenous formulations) for each active ingredient. In addition, such administration also encompasses use of each type of therapeutic agent in a sequential or separate manner, either at approximately the same time or at different times. Regardless of whether the active ingredients are administered as a single formulation or in separate formulations, the drugs are administered to the same patient as part of the same course of therapy. In any case, the treatment regimen will provide beneficial effects in treating the conditions or disorders described herein.

The term "pharmaceutically acceptable" as used herein refers to those compounds, materials, compositions and/or dosage forms, which are, within the scope of sound medical judgment, suitable for contact with the tissues a warm-blooded animal, e.g., a mammal or human, without excessive toxicity, irritation allergic response and other problem complications commensurate with a reasonable benefit/risk ratio.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

The terms "fixed combination," "fixed dose," and "single formulation" as used herein refers to a single carrier or vehicle or dosage form formulated to deliver an amount, which is jointly therapeutically effective for the treatment of cancer, of both therapeutic agents to a patient. The single vehicle is designed to deliver an amount of each of the agents, along with any pharmaceutically acceptable carriers or excipients. In some embodiments, the vehicle is a tablet, capsule, pill, or a patch. In other embodiments, the vehicle is a solution or a suspension.

The term "non-fixed combination," "kit of parts," and "separate formulations" means that the active ingredients, i.e., the HDAC6 inhibitor and the aurora kinase inhibitor, are administered to a patient as separate entities either simultaneously, concurrently or sequentially with no specific time limits, wherein such administration provides therapeutically effective levels of the two compounds in the body of the subject in need thereof. The latter also applies to cocktail therapy, e.g., the administration of three or more active ingredients.

An "oral dosage form" includes a unit dosage form prescribed or intended for oral administration. In an embodiment of the pharmaceutical combinations provided herein, the HDAC6 inhibitor (e.g., Compounds A or B) is administered as an oral dosage form.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer.

The term "prevent," "preventing," or "prevention" as used herein comprises the prevention of at least one symptom associated with or caused by the state, disease or disorder being prevented.

The term "pharmaceutically effective amount," "therapeutically effective amount," or "clinically effective amount" of a combination of therapeutic agents is an amount sufficient to provide an observable or clinically significant improvement over the baseline clinically observable signs and symptoms of the disorders treated with the combination.

The term "jointly therapeutically active" or "joint therapeutic effect" as used herein means that the therapeutic agents can be given separately (in a chronologically staggered manner, especially a sequence-specific manner) in such time intervals that they prefer, in the warm-blooded animal, especially human, to be treated, still show an (preferably synergistic) interaction (joint therapeutic effect). Whether this is the case can, inter alia, be determined by following the blood levels of the compounds, showing that both compounds are present in the blood of the human to be treated at least during certain time intervals.

The term "synergistic effect" as used herein, refers to action of two agents such as, for example, a compound of Formula I or a pharmaceutically acceptable salt thereof, and an aurora kinase inhibitor (e.g., alisertib), to produce an effect, for example, slowing the symptomatic progression of cancer or symptoms thereof, which is greater than the simple addition of the effects of each drug administered by itself. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively. The pharmaceutical combinations provided herein, exhibit synergistic effects in connection with cell growth and viability in connection with myeloma and lymphoma cell lines (see, e.g., Examples 5 and 6)

As used herein, the term "resistant" or "refractive" to a therapeutic agent when referring to a cancer patient means that the cancer has innate, or achieved resistance to, the effects of the therapeutic agent as a result of contact with the therapeutic agent. Stated alternatively, the cancer is resistant to the ordinary standard of care associated with the particular therapeutic agent.

The term "subject" or "patient" as used herein is intended to include animals, which are capable of suffering from or afflicted with a cancer or any disorder involving, directly or indirectly, a cancer. Examples of subjects include mammals, e.g., humans, apes, monkeys, dogs, cows, horses, pigs, sheep, goats, cats, mice, rabbits, rats, and transgenic non-human animals. In an embodiment, the subject is a human, e.g., a human suffering from, at risk of suffering from, or potentially capable of suffering from cancers.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The terms "about" or "approximately" are generally understood by persons knowledgeable in the relevant subject area, but in certain circumstances can mean within 20%, within 10%, or within 5% of a given value or range. Alternatively, especially in biological systems, the term "about" means within about a log (i.e., an order of magnitude) or within a factor of two of a given value. The term "histone deacetylase" or "HDAC" refers to enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "histone deacetylase inhibitor" (HDAC inhibitors, HDACi, HDIs) as used herein refers to a compound that selectively targets, decreases, or inhibits at least one activity of a histone deacetylase.

Histone Deacetylase Inhibitors

Provided herein are pharmaceutical combinations comprising a histone deacetylase 6 (HDAC6) inhibitor of Formula I (also referred to herein as "compounds of Formula I"):

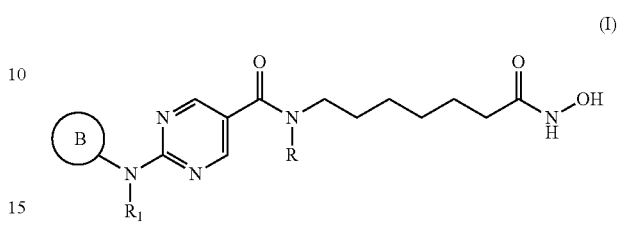

(I)

or a pharmaceutically acceptable salt thereof,
wherein,
ring B is aryl or heteroaryl;
$R_1$ is aryl or heteroaryl, each of which may be optionally substituted by OH, halo, or $C_{1-6}$-alkyl;
and
R is H or $C_{1-6}$-alkyl.

In an embodiment of the compound of Formula I, ring B is aryl. In various embodiments, $R^1$ is aryl or heteroaryl, each of which may be optionally substituted by halo.

In an embodiment of Formula I, $R_1$ is an aryl that is substituted by OH, halo, or $C_{1-6}$-alkyl.

In another embodiment of Formula I, $R_1$ is $C_5$-$C_7$ aryl that is substituted by OH, halo, or $C_{1-6}$-alkyl.

In another embodiment of Formula I, $R_1$ is $C_4$-$C_7$ heteroaryl that is substituted by OH, halo, or $C_{1-6}$-alkyl.

In yet another embodiment of Formula I, $R_1$ is phenyl that is substituted by OH, halo, or $C_{1-6}$-alkyl.

In yet another embodiment of Formula I, $R_1$ is phenyl that is substituted by chloro.

In yet another embodiment of Formula I, $R_1$ is phenyl that is substituted by halo.

In another embodiment of Formula I, ring B is $C_5$-$C_7$ aryl.

In another embodiment of Formula I, ring B is $C_4$-$C_7$ heteroaryl.

In yet another embodiment of Formula I, ring B is phenyl.

In a specific embodiment, the compound of Formula I is Compound A, or a pharmaceutically acceptable salt thereof, or Compound B, or a pharmaceutically acceptable salt thereof, as shown in Table 1:

TABLE 1

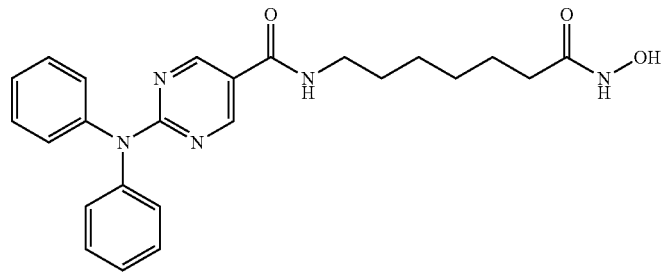

Compound A
2-(diphenylamino)-N-(7-(hydroxyamino)-7-oxoheptyl)pyrimidine-5-carboxamide
$IC_{50}$(nM) HDAC6 = 10 HDAC3 = 84

TABLE 1-continued

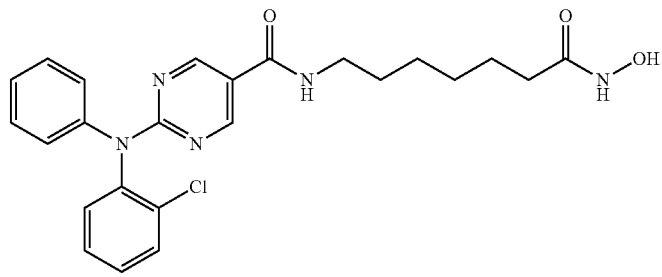

Compound B
2-((2-chlorophenyl)(phenyl)amino)-N-(7-
(hydroxyamino)-7-oxoheptyl)pyrimidine-5-
carboxamide
$IC_{50}$(nM) HDAC6 = 4 HDAC3 = 76

For convenience, the group of the histone deacetylase 6 inhibitors of Formula I and its salts are collectively referred to as compounds of Formula I, meaning that reference to compounds of Formula I will refer to any of the compounds or pharmaceutically acceptable salt thereof in the alternative.

Compounds of Formula I (e.g., Compounds A and B) are known HDAC6 inhibitors, and are described in PCT Pub. No. WO2011/091213, the content of which is incorporated herein by reference in its entirety. Compounds A and B are currently being investigated in Phase 1b clinical development for the treatment of multiple myeloma.

The preparation of Compounds A and B are also described herein as Example 1. Preferably, Compounds A and B are in the free base form.

The salts of compounds of Formula I are preferably pharmaceutically acceptable salts; suitable counter-ions forming pharmaceutically acceptable salts are known in the field.

Aurora Kinase Inhibitors

The term "aurora kinase inhibitor" as used herein refers to a compound that selectively targets, decreases, or inhibits at least one activity of an aurora kinase. Disorders associated with misregulated Aurora kinase activity, are, e.g., solid tumor cancers including lung cancer, breast cancer, colon cancer, ovarian cancer, melanoma, and pancreatic cancer, as well as hematological cancers including leukemia and lymphomas, AML, ALL, and CML (see, e.g., Gavriilidis, P. et al., J. Clin. Med. Res. 2015; 7(10):742-751).

Non-limiting examples of aurora kinase inhibitors include, e.g., alisertib, AT-9283, barasertib, ENMD-2076, MK-5108, MSC 1992371A, danusertib, and tozasertib, or pharmaceutically acceptable salts thereof. The structures of these compounds are found in Table 2 (Choudary, et al. Ther. Adv. Hematol. 6:282. 2015).

TABLE 2

| Drug | Compound | Selectivity | Indications |
|---|---|---|---|
| Alisertib | | Aurora A | MM, NHL, CML, AML and solid tumors |

TABLE 2-continued
| Drug | Compound | Selectivity | Indications |
|---|---|---|---|
| AT-9283 | 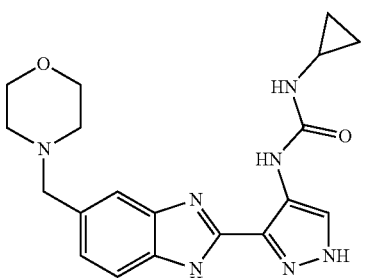 | Aurora A and Aurora B | CML, AML and solid tumors |
| Barasertib | 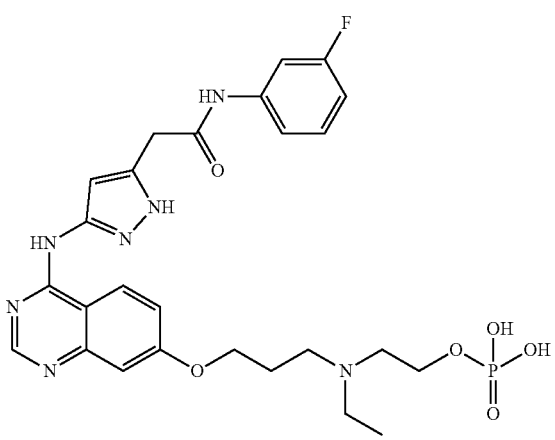 [SMILES: CCN(CCCOc1ccc2c(Nc3cc(CC(=O)Nc4cccc(F)c4)[nH]n3)ncnc2c1)CCOP(=O)(O)O] | Aurora B | AML and solid tumors |
| ENMD-2076 | 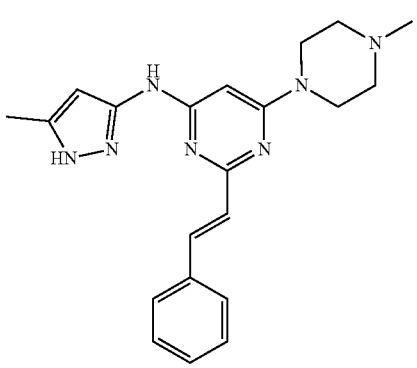 | Aurora A | MM, AML and solid tumors |
| MK-5108 | 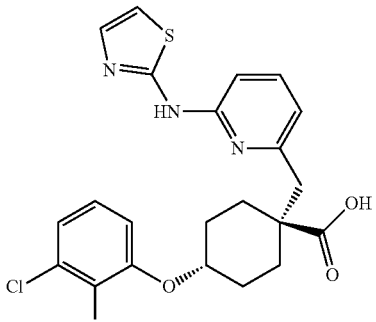 | Aurora A | NHL and solid tumors |

TABLE 2-continued

| Drug | Compound | Selectivity | Indications |
|---|---|---|---|
| MSC 1992371A | 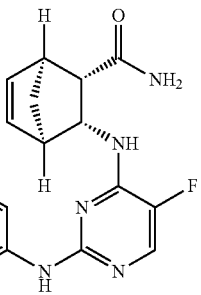 | Pan | AML and CML |
| Danusertib | 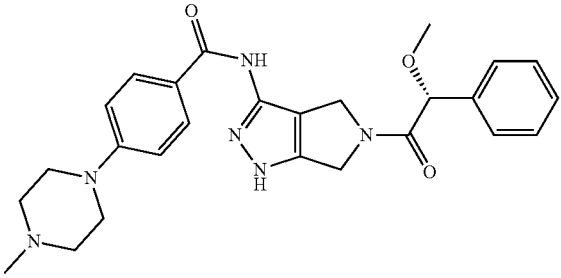 [SMILES: CO[C@@H](C(=O)N1Cc2[nH]nc(NC(=O)c3ccc(N4CCN(C)CC4)cc3)c2C1)c1ccccc1] | Pan | MM, CML and solid tumors |
| Tozasertib | 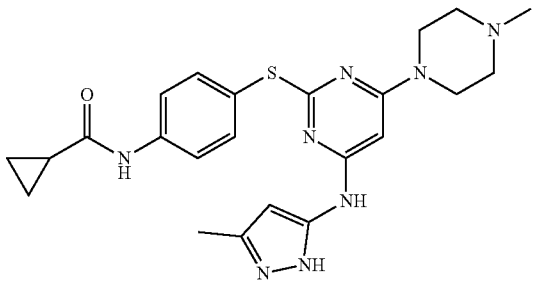 [SMILES: Cc1cc(Nc2cc(N3CCN(C)CC3)nc(Sc3ccc(NC(=O)C4CC4)cc3)n2)[nH]n1] | Pan | MM, AML and solid tumors |

Any of these aurora kinase inhibitors can be used in the pharmaceutical combinations provided herein. In a particular embodiment, the aurora kinase inhibitor is alisertib, or a pharmaceutically acceptable salt thereof. Clinical trials investigating alisertib in various types of solid tumors, including, e.g., breast cancer, small-cell lung cancer, non-small cell lung cancer, head and neck squamous-cell carcinoma, and gastro-oesophageal adenocarcinoma have been completed (Melichar, B, et al., The Lancet Oncology, Vol. 16, No. 4, p. 395-405, April 2015).

Accordingly, in various embodiments of the pharmaceutical combination, the aurora kinase inhibitor is selected from the group consisting of alisertib, AT-9283, barasertib, ENMD-2076, MK-5108, MSC 1992371A, danusertib, and tozasertib, or pharmaceutically acceptable salts thereof. In a particular embodiment, the aurora kinase inhibitor is alisertib, or a pharmaceutically acceptable salt thereof. In an embodiment, the aurora kinase inhibitor is AT-9283, or a pharmaceutically acceptable salt thereof. In an embodiment, the aurora kinase inhibitor is barasertib, or a pharmaceutically acceptable salt thereof. In an embodiment, the aurora kinase inhibitor is ENMD-2076, or a pharmaceutically acceptable salt thereof. In an embodiment, the aurora kinase inhibitor is MK-5108, or a pharmaceutically acceptable salt thereof. In an embodiment, the aurora kinase inhibitor is MSC 1992371A, or a pharmaceutically acceptable salt thereof. In an embodiment, the aurora kinase inhibitor is danusertib, or a pharmaceutically acceptable salt thereof. In an embodiment, the aurora kinase inhibitor is tozasertib, or a pharmaceutically acceptable salt thereof.

Data provided herein shows that the combination therapy provided herein (e.g., HDAC6 inhibitors and an aurora kinase inhibitor) synergistically suppressed cancer cell growth (See, e.g., Examples 5 and 6). Further, the combination therapy provided herein increases apoptosis to a more significant extent relative to either single agent alone (see, e.g., Examples 7 and 8).

Compounds of Formula I or the aurora kinase inhibitor, or both, can be administered in free form or in pharmaceutically acceptable salt form.

Unless otherwise specified, or clearly indicated by the text, reference to therapeutic agents useful in the pharmaceutical combination provided herein includes both the free base of the compounds, and all pharmaceutically acceptable salts of the compounds.

Also provided herein is a commercial package comprising, as therapeutic agents, the pharmaceutical combination provided herein, together with instructions for simultaneous, separate or sequential administration thereof for use in the delay of progression or treatment of a cancer.

Methods for Treating

Provided herein is a method for treating or preventing cancer in a subject in need thereof comprising administering to the subject a therapeutically effective amount of a pharmaceutical combination provided herein, i.e., a pharmaceutical combination comprising:
(a) a histone deacetylase 6 (HDAC6) inhibitor of Formula I:

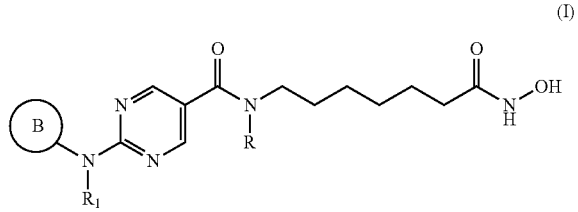

or a pharmaceutically acceptable salt thereof,
wherein,
ring B is aryl or heteroaryl;
R₁ is aryl or heteroaryl, each of which may be optionally substituted by OH, halo, or $C_{1-6}$-alkyl;
and
R is H or $C_{1-6}$-alkyl; and
(b) an aurora kinase inhibitor, or a pharmaceutically acceptable salt thereof.

In an embodiment, provided herein is a method for treating cancer in a subject in need thereof comprising administering to the subject a therapeutically effective amount of a pharmaceutical combination provided herein.

In a specific embodiment of the methods provided herein, the HDAC6 inhibitor is Compound A, or a pharmaceutically acceptable salt thereof; and the aurora kinase inhibitor is alisertib, or a pharmaceutically acceptable salt thereof.

In another specific embodiment of the methods provided herein, the HDAC6 inhibitor is Compound B, or a pharmaceutically acceptable salt thereof; and the aurora kinase inhibitor is alisertib, or a pharmaceutically acceptable salt thereof.

The method provided herein can be used for both solid tumors and liquid tumors. Further, depending on the tumor type and particular combination used, a decrease of the tumor volume can be obtained. The combination disclosed herein is also suited to prevent the metastatic spread of tumors and the growth or development of micrometastases. The combination disclosed herein is suitable for the treatment of poor prognosis patients.

In an embodiment of any of the method provided herein, the cancer is selected from a benign or malignant tumor of the lung (including small cell lung cancer and non-small-cell lung cancer), bronchus, prostate, breast (including sporadic breast cancers and sufferers of Cowden disease), pancreas, gastrointestinal tract, colon, rectum, colon carcinoma, colorectal cancer, thyroid, liver, biliary tract, intrahepatic bile duct (including cholangiocarcinoma), hepatocellular, adrenal gland, stomach, gastric, glioma, CNS (including glioblastoma, astrocytomas, and ependymomas), endometrial, kidney, renal pelvis, bladder, uterus, cervix, vagina, ovary, multiple myeloma, esophagus, neck or head, brain, oral cavity and pharynx, larynx, small intestine, a melanoma, villous colon adenoma, a sarcoma, a neoplasia, a neoplasia of epithelial character, a mammary carcinoma, basal cell carcinoma, squamous cell carcinoma, actinic keratosis, polycythemia vera, essential thrombocythemia, a leukemia (including acute myelogenous leukemia (AML), chronic myelogenous leukemia (CML), acute lymphoblastic leukemia (ALL), chronic lymphoblastic leukemia (CLL), myelodysplastic syndromes, megakaryoblastic leukemia, erythroleukemia and myeloid leukemia), a lymphoma (including non-Hodgkin lymphoma (e.g., mantle cell lymphoma or MCL) and Hodgkin's lymphoma), myelofibrosis with myeloid metaplasia, Waldenstrom disease, and Barret's adenocarcinoma.

In various embodiments, the cancer is a lymphoma, leukemia, or myeloma. In particular embodiments, the cancer is non-Hodgkin's lymphoma (NHL), chronic myelogenous leukemia (CML), acute myelogenous leukemia (AML), or multiple myeloma (MM). In further embodiments, the cancer is a T-cell lymphoma or B-cell lymphoma. In yet a further embodiment, the cancer is mantle cell lymphoma (MCL).

In one embodiment, provided herein is a method for treating a cancer in a subject in need thereof, comprising administering to the subject a therapeutically effective amount of an HDAC inhibitor of Formula I, or a pharmaceutically acceptable salt thereof, and a therapeutically effective amount of an aurora kinase inhibitor. In some embodiments, provided herein is a method for treating a cancer in a subject in need thereof, comprising administering to the subject a therapeutically effective amount of Compound A, or a pharmaceutically acceptable salt thereof, and a therapeutically effective amount of an aurora kinase inhibitor.

In another embodiment, provided herein is a method for treating a solid tumor in a subject in need thereof, comprising administering to the subject a therapeutically effective amount of an HDAC inhibitor of Formula I, or a pharmaceutically acceptable salt thereof, and a therapeutically effective amount of an aurora kinase inhibitor, or a pharmaceutically acceptable salt thereof. In some embodiments, provided herein is a method for treating a solid tumor in a subject in need thereof, comprising administering to the subject a therapeutically effective amount of Compound A, or a pharmaceutically acceptable salt thereof, and a therapeutically effective amount of an aurora kinase inhibitor, or a pharmaceutically acceptable salt thereof.

In another embodiment, provided herein is a method for treating a hematological cancer in a subject in need thereof, comprising administering to the subject a therapeutically effective amount of an HDAC inhibitor of Formula I, or a pharmaceutically acceptable salt thereof, and a therapeutically effective amount of an aurora kinase inhibitor, or a pharmaceutically acceptable salt thereof. In some embodiments, provided herein is a method for treating a hematological cancer in a subject in need thereof, comprising administering to the subject a therapeutically effective amount of Compound A, or a pharmaceutically acceptable salt thereof, and a therapeutically effective amount of an aurora kinase inhibitor, or a pharmaceutically acceptable salt thereof.

In another embodiment, provided herein is a method for treating a leukemia in a subject in need thereof, comprising administering to the subject a therapeutically effective amount of an HDAC inhibitor of Formula I, or a pharmaceutically acceptable salt thereof, and a therapeutically effective amount of an aurora kinase inhibitor, or a pharmaceutically acceptable salt thereof. In some embodiments, provided herein is a method for treating a leukemia in a subject in need thereof, comprising administering to the subject a therapeutically effective amount of Compound A, or a pharmaceutically acceptable salt thereof, and a therapeutically effective amount of an aurora kinase inhibitor, or a pharmaceutically acceptable salt thereof.

In another embodiment, provided herein is a method for treating a lymphoma in a subject in need thereof, comprising administering to the subject a therapeutically effective amount of an HDAC inhibitor of Formula I, or a pharmaceutically acceptable salt thereof, and a therapeutically effective amount of an aurora kinase inhibitor, or a pharmaceutically acceptable salt thereof. In some embodiments, provided herein is a method for treating a lymphoma in a subject in need thereof, comprising administering to the subject a therapeutically effective amount of Compound A, or a pharmaceutically acceptable salt thereof, and a therapeutically effective amount of an aurora kinase inhibitor, or a pharmaceutically acceptable salt thereof.

In another embodiment, provided herein is a method for treating a myeloma in a subject in need thereof, comprising administering to the subject a therapeutically effective amount of an HDAC inhibitor of Formula I, or a pharmaceutically acceptable salt thereof, and a therapeutically effective amount of an aurora kinase inhibitor, or a pharmaceutically acceptable salt thereof. In some embodiments, provided herein is a method for treating a myeloma in a subject in need thereof, comprising administering to the subject a therapeutically effective amount of Compound A, or a pharmaceutically acceptable salt thereof, and a therapeutically effective amount of an aurora kinase inhibitor, or a pharmaceutically acceptable salt thereof.

In another embodiment is a method for treating a cancer in a subject in need thereof, comprising administering to the subject a therapeutically effective amount of Compound A, or a pharmaceutically acceptable salt thereof, and a therapeutically effective amount of alisertib, or a pharmaceutically acceptable salt thereof. This embodiment exhibits synergy such that sub-therapeutic amounts of Compound A or of alisertib can be used in the method.

In another embodiment is a method for treating a solid tumor in a subject in need thereof, comprising administering to the subject a therapeutically effective amount of Compound A, or a pharmaceutically acceptable salt thereof, and a therapeutically effective amount of alisertib, or a pharmaceutically acceptable salt thereof.

In another embodiment is a method for treating a hematological cancer in a subject in need thereof, comprising administering to the subject a therapeutically effective amount of Compound A, or a pharmaceutically acceptable salt thereof, and a therapeutically effective amount of alisertib, or a pharmaceutically acceptable salt thereof.

In another embodiment is a method for treating a leukemia in a subject in need thereof, comprising administering to the subject a therapeutically effective amount of Compound A, or a pharmaceutically acceptable salt thereof, and a therapeutically effective amount of alisertib, or a pharmaceutically acceptable salt thereof.

In another embodiment is a method for treating a lymphoma in a subject in need thereof, comprising administering to the subject a therapeutically effective amount of Compound A, or a pharmaceutically acceptable salt thereof, and a therapeutically effective amount of alisertib, or a pharmaceutically acceptable salt thereof.

In another embodiment is a method for treating a myeloma in a subject in need thereof, comprising administering to the subject a therapeutically effective amount of Compound A, or a pharmaceutically acceptable salt thereof, and a therapeutically effective amount of alisertib, or a pharmaceutically acceptable salt thereof.

In yet another embodiment is a method for treating a cancer in a subject in need thereof, comprising administering to the subject a therapeutically effective amount of Compound A, or a pharmaceutically acceptable salt thereof, and a therapeutically effective amount of an aurora kinase inhibitor selected from the group consisting of alisertib, AT-9283, barasertib, ENMD-2076, MK-5108, MSC 1992371A, danusertib, and tozasertib, or pharmaceutically acceptable salts thereof.

In other embodiments, provided herein is a method for treating a cancer in a subject in need thereof, comprising administering to the subject a therapeutically effective amount of Compound B, or a pharmaceutically acceptable salt thereof, and a therapeutically effective amount of an aurora kinase inhibitor, or a pharmaceutically acceptable salt thereof. In some embodiments, the method comprises administering to the subject a therapeutically effective amount of Compound B, or a pharmaceutically acceptable salt thereof, and a therapeutically effective amount of an aurora kinase inhibitor selected from the group consisting of alisertib, AT-9283, barasertib, ENMD-2076, MK-5108, MSC 1992371A, danusertib, and tozasertib, or pharmaceutically acceptable salts thereof.

In another embodiment, provided herein is a method for treating a solid tumor in a subject in need thereof, comprising administering to the subject a therapeutically effective amount of an HDAC inhibitor of Formula I, or a pharmaceutically acceptable salt thereof, and a therapeutically effective amount of an aurora kinase inhibitor, or a pharmaceutically acceptable salt thereof. In some embodiments, provided herein is a method for treating a solid tumor in a subject in need thereof, comprising administering to the subject a therapeutically effective amount of Compound B, or a pharmaceutically acceptable salt thereof, and a therapeutically effective amount of an aurora kinase inhibitor, or a pharmaceutically acceptable salt thereof.

In another embodiment, provided herein is a method for treating a hematological cancer in a subject in need thereof, comprising administering to the subject a therapeutically effective amount of an HDAC inhibitor of Formula I, or a pharmaceutically acceptable salt thereof, and a therapeutically effective amount of an aurora kinase inhibitor, or a pharmaceutically acceptable salt thereof. In some embodiments, provided herein is a method for treating a hematological cancer in a subject in need thereof, comprising administering to the subject a therapeutically effective amount of Compound B, or a pharmaceutically acceptable salt thereof, and a therapeutically effective amount of an aurora kinase inhibitor, or a pharmaceutically acceptable salt thereof.

In another embodiment, provided herein is a method for treating a leukemia in a subject in need thereof, comprising administering to the subject a therapeutically effective amount of an HDAC inhibitor of Formula I, or a pharmaceutically acceptable salt thereof, and a therapeutically effective amount of an aurora kinase inhibitor, or a pharmaceutically acceptable salt thereof. In some embodiments, provided herein is a method for treating a leukemia in a subject in need thereof, comprising administering to the subject a therapeutically effective amount of Compound B, or a pharmaceutically acceptable salt thereof, and a therapeutically effective amount of an aurora kinase inhibitor, or a pharmaceutically acceptable salt thereof.

In another embodiment, provided herein is a method for treating a lymphoma in a subject in need thereof, comprising administering to the subject a therapeutically effective amount of an HDAC inhibitor of Formula I, or a pharmaceutically acceptable salt thereof, and a therapeutically effective amount of an aurora kinase inhibitor, or a pharmaceutically acceptable salt thereof. In some embodiments, provided herein is a method for treating a lymphoma in a subject in need thereof, comprising administering to the subject a therapeutically effective amount of Compound B, or a pharmaceutically acceptable salt thereof, and a therapeutically effective amount of an aurora kinase inhibitor, or a pharmaceutically acceptable salt thereof.

In another embodiment, provided herein is a method for treating a myeloma in a subject in need thereof, comprising administering to the subject a therapeutically effective amount of an HDAC inhibitor of Formula I, or a pharmaceutically acceptable salt thereof, and a therapeutically effective amount of an aurora kinase inhibitor, or a pharmaceutically acceptable salt thereof. In some embodiments, provided herein is a method for treating a myeloma in a subject in need thereof, comprising administering to the subject a therapeutically effective amount of Compound B, or a pharmaceutically acceptable salt thereof, and a therapeutically effective amount of an aurora kinase inhibitor, or a pharmaceutically acceptable salt thereof.

In another embodiment is a method for treating a cancer in a subject in need thereof, comprising administering to the subject a therapeutically effective amount of Compound B, or a pharmaceutically acceptable salt thereof, and a therapeutically effective amount of alisertib, or a pharmaceutically acceptable salt thereof. This embodiment exhibits synergy such that sub-therapeutic amounts of Compound B or of alisertib can be used in the method.

In another embodiment is a method for treating a solid tumor in a subject in need thereof, comprising administering to the subject a therapeutically effective amount of Compound B, or a pharmaceutically acceptable salt thereof, and a therapeutically effective amount of alisertib, or a pharmaceutically acceptable salt thereof.

In another embodiment is a method for treating a hematological cancer in a subject in need thereof, comprising administering to the subject a therapeutically effective amount of Compound B, or a pharmaceutically acceptable salt thereof, and a therapeutically effective amount of alisertib, or a pharmaceutically acceptable salt thereof.

In another embodiment is a method for treating a leukemia in a subject in need thereof, comprising administering to the subject a therapeutically effective amount of Compound B, or a pharmaceutically acceptable salt thereof, and a therapeutically effective amount of alisertib, or a pharmaceutically acceptable salt thereof.

In another embodiment is a method for treating a lymphoma in a subject in need thereof, comprising administering to the subject a therapeutically effective amount of Compound B, or a pharmaceutically acceptable salt thereof, and a therapeutically effective amount of alisertib, or a pharmaceutically acceptable salt thereof.

In another embodiment is a method for treating a myeloma in a subject in need thereof, comprising administering to the subject a therapeutically effective amount of Compound B, or a pharmaceutically acceptable salt thereof, and a therapeutically effective amount of alisertib, or a pharmaceutically acceptable salt thereof.

The subject considered herein is typically a human. However, the subject can be any mammal for which treatment is desired. Thus, the methods described herein can be applied to both human and veterinary applications.

In various embodiments of the pharmaceutical combination, the cancer is a solid tumor. In particular embodiments, the cancer is lung cancer (e.g., small cell lung cancer).

In various embodiments, the cancer is resistant or refractory to treatment with at least one prior therapy.

Pharmaceutical Combinations and Compositions

Provided herein is a pharmaceutical combination comprising a histone deacetylase inhibitor (HDAC) inhibitor and an aurora kinase inhibitor.

In an aspect, provided herein is a pharmaceutical combination comprising:
(a) a histone deacetylase 6 (HDAC6) inhibitor of Formula I:

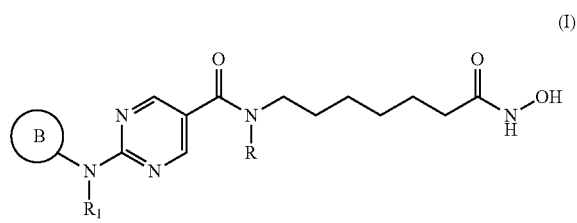

or a pharmaceutically acceptable salt thereof,
wherein,
ring B is aryl or heteroaryl;
$R_1$ is aryl or heteroaryl, each of which may be optionally substituted by OH, halo, or $C_{1-6}$-alkyl;
and
R is H or $C_{1-6}$-alkyl; and
(b) an aurora kinase inhibitor, or a pharmaceutically acceptable salt thereof.

In various embodiments of the pharmaceutical combination, ring B is aryl.

In various embodiments of the pharmaceutical combination, $R_1$ is aryl or heteroaryl, each of which may be optionally substituted by halo.

In various embodiments of the pharmaceutical combination, the compound of Formula I is Compound A, or a pharmaceutically acceptable salt thereof. In another embodiment, the compound of Formula I is Compound B, or a pharmaceutically acceptable salt thereof.

In various embodiments of the pharmaceutical combination, the aurora kinase inhibitor is selected from the group consisting of alisertib, AT-9283, barasertib, ENMD-2076, MK-5108, MSC 1992371A, danusertib, and tozasertib, or pharmaceutically acceptable salts thereof. In a particular embodiment, the aurora kinase inhibitor is alisertib, or a pharmaceutically acceptable salt thereof.

In a specific embodiment of the pharmaceutical combination, the HDAC6 inhibitor is Compound A, or a pharmaceutically acceptable salt thereof; and the aurora kinase inhibitor is alisertib, or a pharmaceutically acceptable salt thereof.

In another specific embodiment of the pharmaceutical combination, the HDAC6 inhibitor is Compound B, or a pharmaceutically acceptable salt thereof; and the aurora kinase inhibitor is alisertib, or a pharmaceutically acceptable salt thereof.

In various embodiments of the pharmaceutical combination, the HDAC6 inhibitor and the aurora kinase inhibitor are in the same formulation. Alternatively, the HDAC6 inhibitor and the aurora kinase inhibitor are in separate formulations.

In various embodiments of the pharmaceutical combination, the combination is for simultaneous or sequential administration.

In various embodiments, the pharmaceutical combination is for use in treating or preventing cancer in a subject in need thereof. In a particular embodiment, the pharmaceutical combination is for use in treating cancer in a subject in need thereof.

In an embodiment, the combination provided herein is used for the treatment or prevention of cancer comprising administering to the subject a combination therapy, comprising an effective amount of the HDAC6 inhibitor (i.e., compounds of Formula I) and an effective amount of the aurora kinase inhibitor. Preferably, these compounds are administered at therapeutically effective dosages which, when combined, provide a beneficial effect. The administration can comprise the separate administration of each component, either simultaneously, or sequentially.

In various embodiments, the pharmaceutical combination is for use in the preparation of a medicament for the treatment or prevention of cancer. In a further embodiment, the pharmaceutical combination is for use in the preparation of a medicament for the treatment of cancer.

The pharmaceutical combination provided herein can also inhibit the growth of both solid tumors and liquid tumors. Further, depending on the tumor type and particular combination used, a decrease of the tumor volume can be obtained. The combination disclosed herein is also suited to prevent the metastatic spread of tumors and the growth or development of micrometastases. The combination disclosed herein is suitable for the treatment of poor prognosis patients.

In an embodiment of any of the pharmaceutical combinations provided herein, the cancer is selected from a benign or malignant tumor of the lung (including small cell lung cancer and non-small-cell lung cancer), bronchus, prostate, breast (including sporadic breast cancers and sufferers of Cowden disease), pancreas, gastrointestinal tract, colon, rectum, colon carcinoma, colorectal cancer, thyroid, liver, biliary tract, intrahepatic bile duct (including cholangiocarcinoma), hepatocellular, adrenal gland, stomach, gastric, glioma, CNS (including glioblastoma, astrocytomas, and ependymomas), endometrial, kidney, renal pelvis, bladder, uterus, cervix, vagina, ovary, multiple myeloma, esophagus, neck or head, brain, oral cavity and pharynx, larynx, small intestine, a melanoma, villous colon adenoma, a sarcoma, a neoplasia, a neoplasia of epithelial character, a mammary carcinoma, basal cell carcinoma, squamous cell carcinoma, actinic keratosis, polycythemia vera, essential thrombocythemia, a leukemia (including acute myelogenous leukemia (AML), chronic myelogenous leukemia (CML), acute lymphoblastic leukemia (ALL), chronic lymphoblastic leukemia (CLL), myelodysplastic syndromes, megakaryoblastic leukemia, erythroleukemia and myeloid leukemia), a lymphoma (including non-Hodgkin lymphoma (e.g., mantle cell lymphoma or MCL) and Hodgkin's lymphoma), myelofibrosis with myeloid metaplasia, Waldenstrom disease, and Barret's adenocarcinoma.

In various embodiments, the cancer is a lymphoma, leukemia, or myeloma. In particular embodiments, the cancer is non-Hodgkin's lymphoma (NHL), chronic myelogenous leukemia (CML), acute myelogenous leukemia (AML), or multiple myeloma (MM). In further embodiments, the cancer is a T-cell lymphoma or B-cell lymphoma. In yet a further embodiment, the cancer is mantle cell lymphoma (MCL).

In various embodiments of the pharmaceutical combination, the cancer is a solid tumor. In particular embodiments, the cancer is lung cancer (e.g., small cell lung cancer).

In various embodiments, the cancer is resistant or refractory to treatment with at least one prior therapy.

Provided herein are pharmaceutical compositions comprising a histone deacetylase inhibitor (HDAC) inhibitor and an aurora kinase inhibitor.

As used herein, term "pharmaceutical composition" is defined herein to refer to a mixture or solution containing the therapeutic agent(s) to be administered to a subject, e.g., a mammal or human, in order to prevent or treat a particular disease or condition affecting the mammal.

In an aspect, provided herein is a pharmaceutical composition comprising
(a) a histone deacetylase 6 (HDAC6) inhibitor of Formula I:

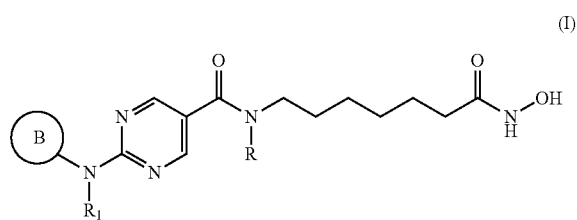

or a pharmaceutically acceptable salt thereof,
wherein,
ring B is aryl or heteroaryl;
$R_1$ is aryl or heteroaryl, each of which may be optionally substituted by OH, halo, or $C_{1-6}$-alkyl;
and
R is H or $C_{1-6}$-alkyl; and
(b) an aurora kinase inhibitor.

In an embodiment of the composition, ring B is aryl. In various embodiments, $R_1$ is aryl or heteroaryl, each of which may be optionally substituted by halo.

In another embodiment of the composition, the HDAC6 inhibitor is Compound A, or a pharmaceutically acceptable salt thereof. In another embodiment of the composition, the HDAC6 inhibitor is Compound B, or a pharmaceutically acceptable salt thereof.

In a specific embodiment of the composition provided herein, the HDAC6 inhibitor is Compound A, or a pharmaceutically acceptable salt thereof; and the aurora kinase inhibitor is alisertib, or a pharmaceutically acceptable salt thereof.

In another specific embodiment of the composition provided herein, the HDAC6 inhibitor is Compound B, or a pharmaceutically acceptable salt thereof; and the aurora kinase inhibitor is alisertib, or a pharmaceutically acceptable salt thereof.

In various embodiments of pharmaceutical composition, the aurora kinase inhibitor is selected from the group consisting of alisertib, AT-9283, barasertib, ENMD-2076, MK-5108, MSC 1992371A, danusertib, and tozasertib, or pharmaceutically acceptable salts thereof. In particular embodiments, the aurora kinase inhibitor is alisertib, or a pharmaceutically acceptable salt thereof.

In an embodiment of the composition, the pharmaceutical composition further comprises one or more excipients. As used herein, the term "pharmaceutically acceptable excipient" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The pharmaceutical composition may contain, from about 0.1% to about 99.9%, preferably from about 1% to about 60%, of the therapeutic agent(s).

Suitable pharmaceutical compositions for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of various conventional mixing, comminution, direct compression, granulating, sugar-coating, dissolving, lyophilizing processes, melt granulation, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units.

Administration/Dose

The method of treating cancer according to the disclosure provided herein can comprise (i) administration of the HDAC6 inhibitor (a) in free or pharmaceutically acceptable salt form and (ii) administration of the aurora kinase inhibitor (b) in free or pharmaceutically acceptable salt form simultaneously or sequentially, in any order, in jointly therapeutically effective amounts, preferably in synergistically effective amounts, e.g., in daily or intermittent dosages. The individual combination partners of the pharmaceutical combination provided herein can be administered separately at different times during the course of therapy or concurrently in divided or single combination forms. The method provided herein is therefore to be understood as embracing all such regimens of simultaneous or alternating treatment and the term "administering" is to be interpreted accordingly.

For example, in one embodiment of the method, the HDAC6 inhibitor is administered first, followed by the aurora kinase inhibitor. In another embodiment of the method, the aurora kinase inhibitor is administered first, followed by the HDAC6 inhibitor.

Compounds of Formula I can be orally administered in an amount from about 10 mg to about 1000 mg (including e.g., about 10 mg to about 500 mg) per day in single or multiple doses. Thus, in an embodiment of the methods of treatment provided herein, the compound of Formula I is administered at a dosage of about 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, or 500 mg per day. In a further embodiment, the compound of Formula I is administered at a dosage of about 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, or 200 mg per day.

In an embodiment of the pharmaceutical combination, Compound A is in an amount from 600 mg to 3000 mg (e.g., about 600, about 800, about 1000, about 1200, about 1400, about 1600, about 1800, about 2000 mg). In a further embodiment of the pharmaceutical combination, Compound A is in an amount from 600 mg to 2000 mg. In a preferred embodiment of the pharmaceutical combination, Compound A is in an amount from 180 mg to 480 mg.

In another embodiment of the pharmaceutical combination, Compound A is in an amount from 5 mg to 600 mg (e.g., about 5, about 25, about 50, about 100, about 200, about 300, about 400, about 500, about 600 mg). In yet another embodiment of the pharmaceutical combination Compound A is 10 mg to 200 mg.

In an embodiment of the pharmaceutical combination, Compound B is in an amount from 600 mg to 3000 mg (e.g., about 600, about 800, about 1000, about 1200, about 1400, about 1600, about 1800, about 2000 mg). In a further embodiment of the pharmaceutical combination, Compound B is in an amount from 600 mg to 2000 mg. In a preferred embodiment of the pharmaceutical combination, Compound B is in an amount from 180 mg to 480 mg.

In another embodiment of the pharmaceutical combination, Compound B is in an amount from 5 mg to 600 mg (e.g., about 5, about 25, about 50, about 100, about 200, about 300, about 400, about 500, about 600 mg). In yet another embodiment of the pharmaceutical combination Compound B is 10 mg to 200 mg.

Aurora kinase inhibitors can be administered in an amount from about 10 mg to about 1000 mg (including e.g., about 10 mg to about 500 mg) per day in single or multiple doses. Thus, in an embodiment of the methods of treatment provided herein, the aurora kinase inhibitor is administered at a dosage of about 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, or 500 mg per day.

In a further embodiment, the aurora kinase inhibitor is administered at a dosage of about 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, or 200 mg per day.

In an embodiment of the pharmaceutical combination, alisertib is in an amount from 600 mg to 3000 mg (e.g., about 600, about 800, about 1000, about 1200, about 1400, about 1600, about 1800, about 2000 mg). In a further embodiment of the pharmaceutical combination, alisertib is in an amount from 600 mg to 2000 mg. In a preferred embodiment of the pharmaceutical combination, alisertib is in an amount from 25 mg to 200 mg.

In another embodiment of the pharmaceutical combination, alisertib is in an amount from 5 mg to 600 mg (e.g., about 5, about 25, about 50, about 100, about 200, about 300, about 400, about 500, about 600 mg). In yet another embodiment of the pharmaceutical combination alisertib is 10 mg to 200 mg.

In an embodiment of the pharmaceutical combination, the ratio of the compound of Formula I to the aurora kinase inhibitor is in the range of 700:1-1:40. In another embodiment, the ratio of the compound of Formula I to the aurora kinase inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; 4:1 to 1:1, for example, 4:1, 3:1, 2:1 or 1:1; or 30:1 to 10:1, for example, 30:1, 20:1 or 10:1.

In another embodiment of the pharmaceutical combination, the ratio of Compound A to the aurora kinase inhibitor is in the range of 700:1-1:40. In another embodiment, the ratio of Compound A to the aurora kinase inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; 4:1 to 1:1, for example, 4:1, 3:1, 2:1 or 1:1; or 30:1 to 10:1, for example, 30:1, 20:1 or 10:1.

In another embodiment of the pharmaceutical combination, the ratio of Compound B to the aurora kinase inhibitor is in the range of 700:1-1:40. In another embodiment, the ratio of Compound B to the aurora kinase inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In another embodiment of the pharmaceutical combination, the ratio of Compound A to alisertib is in the range of 700:1-1:40. In another embodiment, the ratio of Compound A to alisertib is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In another embodiment of the pharmaceutical combination, the ratio of Compound B to alisertib is in the range of 700:1-1:40. In another embodiment, the ratio of Compound B to alisertib is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

The nature of cancer is multifactorial, thus under certain circumstances drugs with different mechanisms of action can be combined. However, any combination of therapeutic agents having different modes of action does not necessarily lead to combinations with advantageous effects. The administration of the pharmaceutical combination provided herein may result, not only in a beneficial effect, e.g., a synergistic therapeutic effect, with regard to alleviating, delaying progression of or inhibiting the symptoms, but also in further surprising beneficial effects, e.g. fewer side-effects, more durable response, an improved quality of life or a decreased morbidity, compared with a monotherapy applying only one of the pharmaceutically therapeutic agents used in the combination provided herein.

A further benefit is that lower doses of the therapeutic agents of the combination provided herein can be used, for example, such that the dosages may not only often be smaller, but also may be applied less frequently, or can be used in order to diminish the incidence of side-effects observed with one of the combination partners alone. This is in accordance with the desires and requirements of the patients to be treated.

It can be shown by established test models that a pharmaceutical combination as provided herein results in the beneficial effects described herein before. The person skilled in the art is fully enabled to select a relevant test model to prove such beneficial effects. The pharmacological activity of the pharmaceutical combinations provided herein may, for example, be demonstrated in a clinical study or in an animal model.

In an embodiment, the pharmaceutical combination or composition, or both, provided herein display a synergistic effect.

In a further embodiment, provided herein is a synergistic combination for administration to a subject comprising the combination provided herein, where the dose range of each component corresponds to the synergistic ranges suggested in a suitable tumor model or clinical study.

In determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients may render impractical the use of this form of testing as a primary model for synergy. However, the observation of synergy in certain experiments can be predictive of the effect in other species, and animal models exist may be used to further quantify a synergistic effect. The results of such studies can also be used to predict effective dose ratio ranges and the absolute doses and plasma concentrations.

The effective dosage of each of the combination partners employed in the combination provided herein may vary depending on the particular compound or pharmaceutical composition employed, the mode of administration, the condition being treated, and the severity of the condition being treated. Thus, the dosage regimen of the combination provided herein is selected in accordance with a variety of factors including the route of administration and the renal and hepatic function of the patient.

The optimum ratios, individual and combined dosages, and concentrations of the combination partners (e.g., compound of Formula I and the aurora kinase inhibitor) of the combination provided herein that yield efficacy without toxicity are based on the kinetics of the therapeutic agents' availability to target sites, and are determined using methods known to those of skill in the art.

The effective dosage of each of the combination partners may require more frequent administration of one of the compound(s) as compared to the other compound(s) in the combination. Therefore, to permit appropriate dosing, packaged pharmaceutical products may contain one or more dosage forms that contain the combination of compounds, and one or more dosage forms that contain one of the compounds, but not the other compound(s) of the combination.

When the combination partners, which are employed in the combination provided herein, are applied in the form as marketed as single drugs, their dosage and mode of administration can be in accordance with the information provided on the package insert of the respective marketed drug, if not mentioned herein otherwise.

The optimal dosage of each combination partner for treatment of a cancer can be determined empirically for each individual using known methods and will depend upon a variety of factors, including, though not limited to: the degree of advancement of the disease; the age, body weight, general health, gender and diet of the individual; the time and route of administration; and other medications the individual is taking. Optimal dosages may be established using routine testing and procedures that are well known in the art.

The amount of each combination partner that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage may vary depending on the compound used and the particular condition to be treated or prevented. Patients may generally be monitored for therapeutic effectiveness using assays suitable for the condition being treated or prevented, which will be familiar to those of ordinary skill in the art. The compound of Formula I and the aurora kinase inhibitor can be administered independently, at the same time or separately within time intervals, wherein these time intervals allow that the combination partners show a cooperative, e.g., synergistic, effect.

In various embodiments of the pharmaceutical combination, the HDAC6 inhibitor and the aurora kinase inhibitor are in the same formulation. Alternatively, the HDAC6 inhibitor and the aurora kinase inhibitor are in separate formulations.

In various embodiments of the pharmaceutical combination, the combination is for simultaneous or sequential administration.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EXAMPLES

The following Examples illustrate the invention described above; they are not, however, intended to limit the scope of the invention in any way. The beneficial effects of the pharmaceutical combination of the present invention can also be determined by other test models known as such to the person skilled in the pertinent art.

Example 1

Synthesis of 2-(diphenylamino)-N-(7-(hydroxyamino)-7-oxoheptyl)pyrimidine-5-carboxamide (Compound A) and 2-((2-chlorophenyl)(phenyl)amino)-N-(7-(hydroxyamino)-7-oxoheptyl)pyrimidine-5-carboxamide (Compound B)

I. Synthesis of 2-(diphenylamino)-N-(7-(hydroxyamino)-7-oxoheptyl)pyrimidine-5-carboxamide (Compound A)

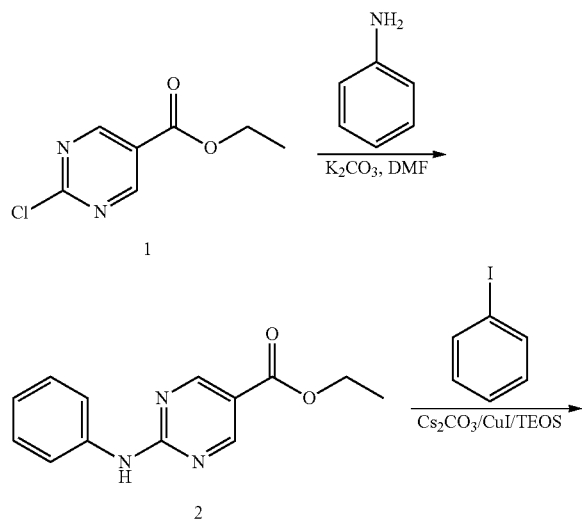

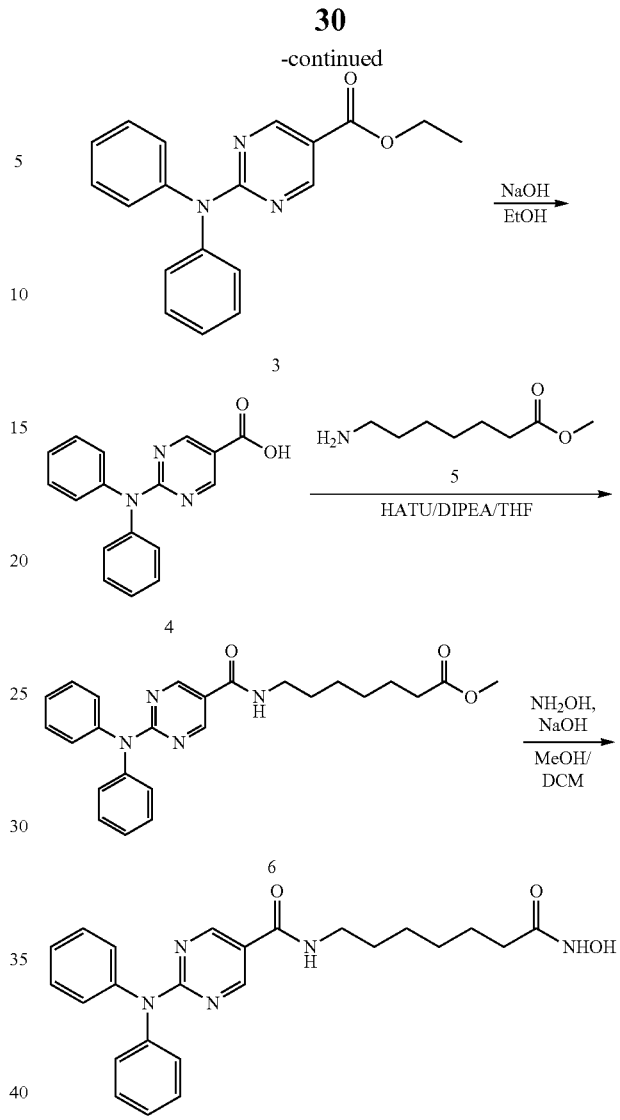

Synthesis of Intermediate 2: A mixture of aniline (3.7 g, 40 mmol), compound 1 (7.5 g, 40 mmol), and $K_2CO_3$ (11 g, 80 mmol) in DMF (100 ml) was degassed and stirred at 120° C. under $N_2$ overnight. The reaction mixture was cooled to r.t. and diluted with EtOAc (200 ml), then washed with saturated brine (200 ml×3). The organic layers were separated and dried over $Na_2SO_4$, evaporated to dryness and purified by silica gel chromatography (petroleum ethers/EtOAc=10/1) to give the desired product as a white solid (6.2 g, 64%).

Synthesis of Intermediate 3: A mixture of compound 2 (6.2 g, 25 mmol), iodobenzene (6.12 g, 30 mmol), CuI (955 mg, 5.0 mmol), $Cs_2CO_3$ (16.3 g, 50 mmol) in TEOS (200 ml) was degassed and purged with nitrogen. The resulting mixture was stirred at 140° C. for 14 hrs. After cooling to r.t., the residue was diluted with EtOAc (200 ml). 95% EtOH (200 ml) and $NH_4F$—$H_2O$ on silica gel [50 g, pre-prepared by the addition of $NH_4F$ (100 g) in water (1500 ml) to silica gel (500 g, 100-200 mesh)] was added, and the resulting mixture was kept at r.t. for 2 hrs. The solidified materials were filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4: 2N NaOH (200 ml) was added to a solution of compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layers were separated, washed with water (2×100 ml), brine (2×100 ml), and dried over Na₂SO₄. Removal of the solvent gave a brown solid (2.5 g, 92%).

Synthesis of Intermediate 6: A mixture of compound 4 (2.5 g, 8.58 mmol), compound 5 (2.52 g, 12.87 mmol), HATU (3.91 g, 10.30 mmol), and DIPEA (4.43 g, 34.32 mmol) was stirred at r.t. overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide: A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at r.t. for 20 min. After removal of the solvent, the mixture was neutralized with 1M HCl to give a white precipitate. The crude product was filtered and purified by pre-H PLC to give a white solid (950 mg, 48%).

II. Synthetic Route 1: 2-((2-chlorophenyl)(phenyl)amino)-N-(7-(hydroxyamino)-7-oxoheptyl)pyrimidine-5-carboxamide (Compound B)

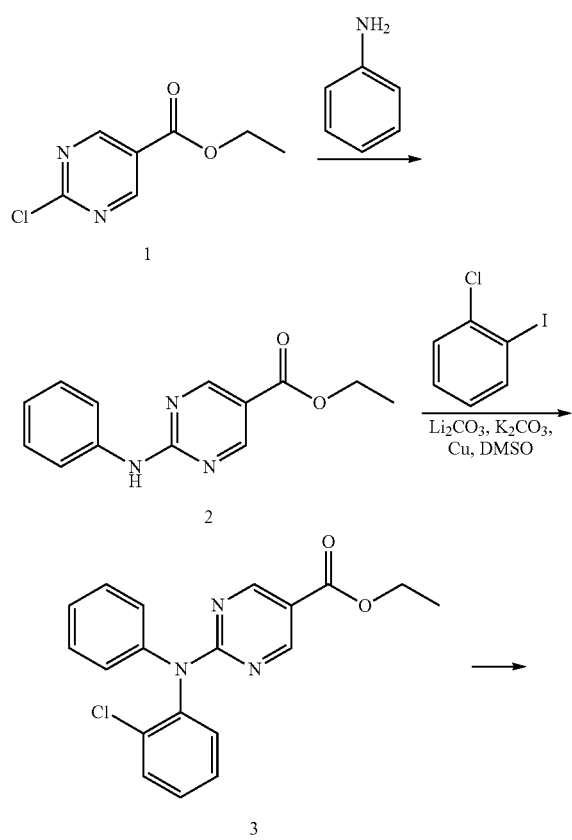

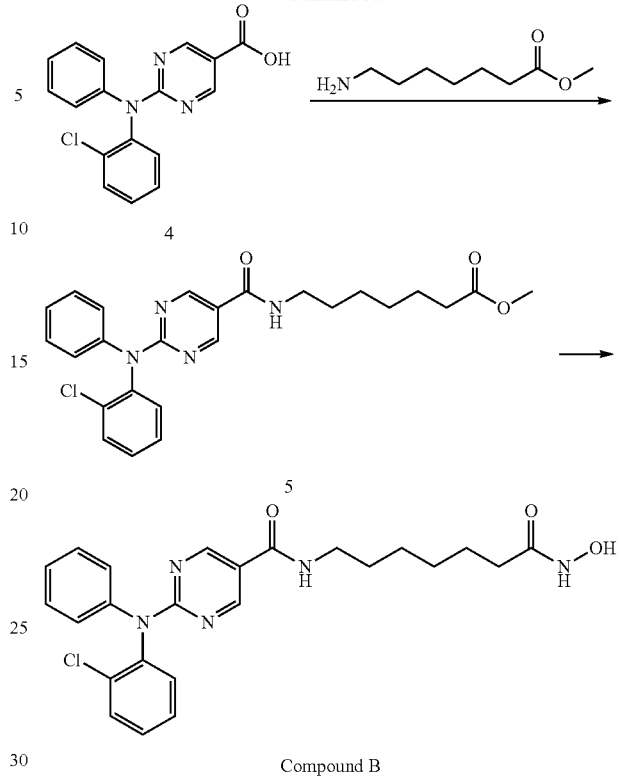

Compound B

Synthesis of Intermediate 2: A mixture of aniline (3.7 g, 40 mmol), ethyl 2-chloropyrimidine-5-carboxylate 1 (7.5 g, 40 mmol), K₂CO₃ (11 g, 80 mmol) in DMF (100 ml) was degassed and stirred at 120° C. under N₂ overnight. The reaction mixture was cooled to rt and diluted with EtOAc (200 ml), then washed with saturated brine (200 ml×3). The organic layer was separated and dried over Na₂SO₄, evaporated to dryness and purified by silica gel chromatography (petroleum ethers/EtOAc=10/1) to give the desired product as a white solid (6.2 g, 64%).

Synthesis of Intermediate 3: A mixture of compound 2 (69.2 g, 1 equiv.), 1-chloro-2-iodobenzene (135.7 g, 2 equiv.), Li₂CO₃ (42.04 g, 2 equiv.), K₂CO₃ (39.32 g, 1 equiv.), Cu (1 equiv. 45 μm) in DMSO (690 ml) was degassed and purged with nitrogen. The resulting mixture was stirred at 140° C. for 36 hours. Work-up of the reaction gave compound 3 at 93% yield.

Synthesis of Intermediate 4: 2N NaOH (200 ml) was added to a solution of the compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layer was separated, washed with water (2×100 ml), brine (2×100 ml), and dried over Na₂SO₄. Removal of solvent gave a brown solid (2.5 g, 92%).

Synthesis of Intermediate 5: A procedure analogous to the Synthesis of Intermediate 6 in Part I of this Example was used.

Synthesis of 2-((2-chlorophenyl)(phenyl)amino)-N-(7-(hydroxyamino)-7-oxoheptyl)pyrimidine-5-carboxamide: A procedure analogous to the Synthesis of 2-(diphenylamino)-N-(7-(hydroxyamino)-7-oxoheptyl)pyrimidine-5-carboxamide in Part I of this Example was used.

III. Synthetic Route 2: 2-((2-chlorophenyl)(phenyl)amino)-N-(7-(hydroxyamino)-7-oxoheptyl)pyrimidine-5-carboxamide (Compound B)

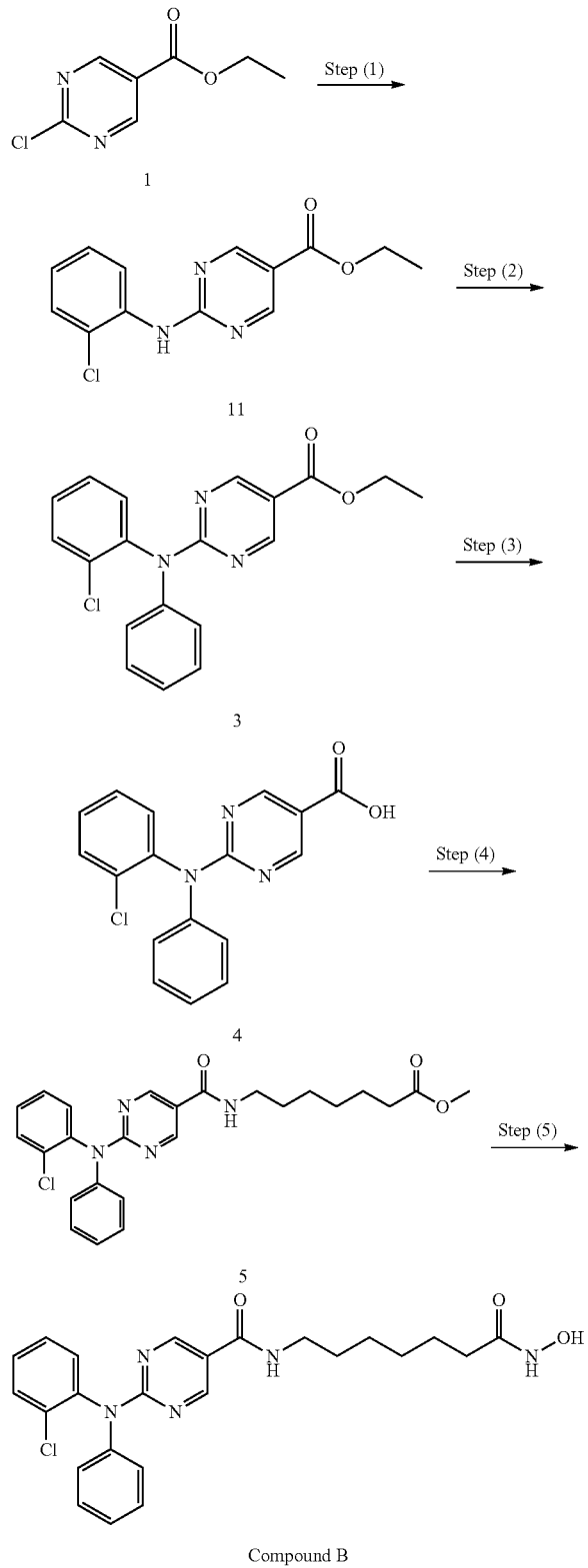

Step (1): Synthesis of Compound 11: Ethyl 2-chloropyrimidine-5-carboxylate (7.0 Kgs), ethanol (60 Kgs), 2-Chloroaniline (9.5 Kgs, 2 eq) and acetic acid (3.7 Kgs, 1.6 eq) were charged to a reactor under inert atmosphere. The mixture was heated to reflux. After at least 5 hours the reaction was sampled for HPLC analysis (method TM-113.1016). When analysis indicated reaction completion, the mixture was cooled to 70±5° C. and N,N-Diisopropylethylamine (DIPEA) was added. The reaction was then cooled to 20±5° C. and the mixture was stirred for an additional 2-6 hours. The resulting precipitate is filtered and washed with ethanol (2×6 Kgs) and heptane (24 Kgs). The cake is dried under reduced pressure at 50±5° C. to a constant weight to produce 8.4 Kgs compound 11 (81% yield and 99.9% purity.

Step (2): Synthesis of Compound 3: Copper powder (0.68 Kgs, 1 eq, <75 micron), potassium carbonate (4.3 Kgs, 1.7 eq), and dimethyl sulfoxide (DMSO, 12.3 Kgs) were added to a reactor (vessel A). The resulting solution was heated to 120±5° C. In a separate reactor (vessel B), a solution of compound 11 (2.9 Kgs) and iodobenzene (4.3 Kgs, 2 eq) in DMSO (5.6 Kgs) was heated at 40±5° C. The mixture was then transferred to vessel A over 2-3 hours. The reaction mixture was heated at 120±5° C. for 8-24 hours, until HPLC analysis (method TM-113.942) determined that 1% compound 11 was remaining.

Step (3): Synthesis of Compound 4: The mixture of Step (2) was cooled to 90-100° C. and purified water (59 Kgs) was added. The reaction mixture was stirred at 90-100° C. for 2-8 hours until HPLC showed that compound 3 was remaining. The reactor was cooled to 25° C. The reaction mixture was filtered through Celite, then a 0.2 micron filter, and the filtrate was collected. The filtrate was extracted with methyl t-butyl ether twice (2×12.8 Kgs). The aqueous layer was cooled to 0-5° C., then acidified with 6N hydrochloric acid (HCl) to pH 2-3 while keeping the temperature<25° C. The reaction was then cooled to 5-15° C. The precipitate was filtered and washed with cold water. The cake was dried at 45-55° C. under reduced pressure to constant weight to obtain 2.2 kg (65% yield) compound 4 in 90.3% AUC purity.

Step (4): Synthesis of Compound 5: Dichloromethane (40.3 Kgs), DMF (33 g, 0.04 eq) and compound 4 (2.3 Kg) were charged to a reaction flask. The solution was filtered through a 0.2 μm filter and was returned to the flask. Oxalyl chloride (0.9 Kgs, 1 eq) was added via addition funnel over 30-120 minutes at <30° C. The batch was then stirred at <30° C. until reaction completion (compound 4≤3%) was confirmed by HPLC (method TM-113.946. Next, the dichloromethane solution was concentrated and residual oxalyl chloride was removed under reduced pressure at <40° C. When HPLC analysis indicated that <0.10% oxalyl chloride was remaining, the concentrate was dissolved in fresh dichloromethane (24 Kgs) and transferred back to the reaction vessel (Vessel A).

A second vessel (Vessel B) was charged with Methyl 7-aminoheptanoate hydrochloride (Compound A1, 1.5 Kgs, 1.09 eq), DI PEA (2.5 Kgs, 2.7 eq), 4 (Dimethylamino) pyridine (DMAP, 42 g, 0.05 eq), and DCM (47.6 Kgs). The mixture was cooled to 0-10° C. and the acid chloride solution in Vessel A was transferred to Vessel B while maintaining the temperature at 5° C. to 10° C. The reaction is stirred at 5-10° C. for 3 to 24 hours at which point HPLC analysis indicated reaction completion (method TM-113.946, compound 4≤5%). The mixture was then extracted with a 1M HCl solution (20 Kgs), purified water (20 Kgs), 7% sodium bicarbonate (20 Kgs), purified water (20 Kgs), and 25% sodium chloride solution (20 Kgs). The dichloromethane was then vacuum distilled at <40° C. and chased repeatedly with isopropyl alcohol. When analysis indicated that <1 mol % DCM was remaining, the mixture was gradually cooled to 0-5° C. and was stirred at 0-5° C. for an at least 2 hours. The resulting precipitate was collected by filtration and washed with cold isopropyl alcohol (6.4 Kgs). The cake was sucked dry on the filter for 4-24 hours, then was further dried at 45-55° C. under reduced pressure to constant weight. 2.2 Kgs (77% yield) was isolated in 95.9% AUC purity method and 99.9 wt %.

Step (5): Synthesis of Compound (I): Hydroxylamine hydrochloride (3.3 Kgs, 10 eq) and methanol (9.6 Kgs) were charged to a reactor. The resulting solution was cooled to 0-5° C. and 25% sodium methoxide (11.2 Kgs, 11 eq) was charged slowly, maintaining the temperature at 0-10° C. Once the addition was complete, the reaction was mixed at 20° C. for 1-3 hours and filtered, and the filter cake was washed with methanol (2×2.1 Kgs). The filtrate (hydroxylamine free base) was returned to the reactor and cooled to 0±5° C. Compound 5 (2.2 Kgs) was added. The reaction was stirred until the reaction was complete (method TM-113.964, compound 5≤2%). The mixture was filtered and water (28 Kgs) and ethyl acetate (8.9 Kgs) were added to the filtrate. The pH was adjusted to 8-9 using 6N HCl then stirred for up to 3 hours before filtering. The filter cake was washed with cold water (25.7 Kgs), then dried under reduced pressure to constant weight. The crude solid compound (I) was determined to be Form IV/Pattern D.

The crude solid (1.87 Kgs) was suspended in isopropyl alcohol (IPA, 27.1 Kg). The slurry was heated to 75±5° C. to dissolve the solids. The solution was seeded with crystals of Compound (I) (Form I/Pattern A), and was allowed to cool to ambient temperature. The resulting precipitate was stirred for 1-2 hours before filtering. The filter cake was rinsed with IPA (2×9.5 Kgs), then dried at 45-55° C. to constant weight under reduced pressure to result in 1.86 kg crystalline white solid Compound (I) in 85% yield and 99.5% purity (AUC %, HPLC method of Table 2).

TABLE 2

| HPLC Method | |
|---|---|
| Column | Zorbax Eclipse XDB-C18, 4.6 mm × 150 mm, 3.5 µm |
| Column Temperature | 40° C. |
| UV Detection Wavelength | Bandwidth 4 nm, Reference off, 272 nm |
| Flow rate | 1.0 mL/min |
| Injection Volume | 10 µL with needle wash |
| Mobile Phase A | 0.05% trifluoroacetic acid (TFA) in purified water |
| Mobile Phase B | 0.04% TFA in acetonitrile |
| Data Collection | 40.0 min |
| Run Time | 46.0 min |

| Gradient | Time (min) | Mobile Phase A | Mobile Phase B |
|---|---|---|---|
| | 0.0 | 98% | 2% |
| | 36.0 | 0% | 100% |
| | 40.0 | 0% | 100% |
| | 40.1 | 98% | 2% |
| | 46.0 | 98% | 2% |

Example 2

HDAC Enzyme Assay

Compound B was tested first by diluting the compound in DMSO to 50 fold the final concentration and a ten point three fold dilution series was made. The compound was diluted in assay buffer (50 mM HEPES, pH 7.4, 100 mM KCl, 0.001% Tween-20, 0.05% BSA, 20 µM TCEP) to 6 fold their final concentration. The HDAC enzymes (purchased from BPS Biosciences; San Diego, CA) were diluted to 1.5 fold their final concentration in assay buffer. The tripeptide substrate and trypsin at 0.05 µM final concentration were diluted in assay buffer at 6 fold their final concentration. The final enzyme concentrations used in these assays were 3.3 ng/ml (HDAC1), 0.2 ng/ml (HDAC2), 0.08 ng/ml (HDAC3) and 2 ng/ml (HDAC6). The final substrate concentrations used were 16 µM (HDAC1), 10 µM (HDAC2), 17 µM (HDAC3) and 14 µM (HDAC6). Five µl of compound and 20 µl of enzyme were added to wells of a black, opaque 384 well plate in duplicate. Enzyme and compound were incubated together at room temperature for 10 minutes. Five µl of substrate was added to each well, the plate was shaken for 60 seconds and placed into a Victor 2 microtiter plate reader. The development of fluorescence was monitored for 60 min and the linear rate of the reaction was calculated. The $IC_{50}$ was determined using Graph Pad Prism by a four parameter curve fit. See Table 1 for $IC_{50}$ associated with Compounds A and B.

Example 3

Microarray Gene Expression Analysis of H929 Cells Treated with Compound A

The Spindle Assembly Checkpoint functions to ensure faithful segregation of genomic DNA during mitosis. The checkpoint is activated while chromosomes are unattached to bipolar spindles. If cells are defective in the Spindle Assembly Checkpoint the cells can bypass the checkpoint and undergo premature division resulting in aneuploidy which can lead to cell death, senescence or enhanced tumorigenesis depending on the severity of aneuploidy.

Microarray gene expression profiling was performed in H929 multiple myeloma (MM) cells to determine whether key mitotic regulators are down regulated by Compound B. H929 multiple myeloma cells were treated for 24 hours or 48 hours with 2, 3, or 4 µM of Compound A. Total RNA was extracted from the cells and subjected to gene expression profiling using an Affymetrix microarray system (Santa Clara, CA). FIG. 1 shows data for the relative fold induction for the Compound A treated cells as compared to DMSO treated cells for each individual probe set representing gene transcripts of survivin, Aurora A, Aurora B, BubR1, CDC20 and MAD2L1. Each of these genes is part of the spindle assembly checkpoint, and the results show that treatment with Compound A reduced the expression of these key mitotic regulatory genes, suggesting treatment with Compound A impacts the function of the spindle assembly checkpoint.

Example 4 qPCR Analysis of Mitotic Regulator Downregulation by Compound A Across MM and Mantle Cell Lymphoma (MCL) Cell Lines Independent qPCR validation of mitotic regulator downregulation by Compound A across MM and MCL cell lines was performed using H929 MM, U266 MM and Jeko-1 MCL cell lines.

Figure 2:
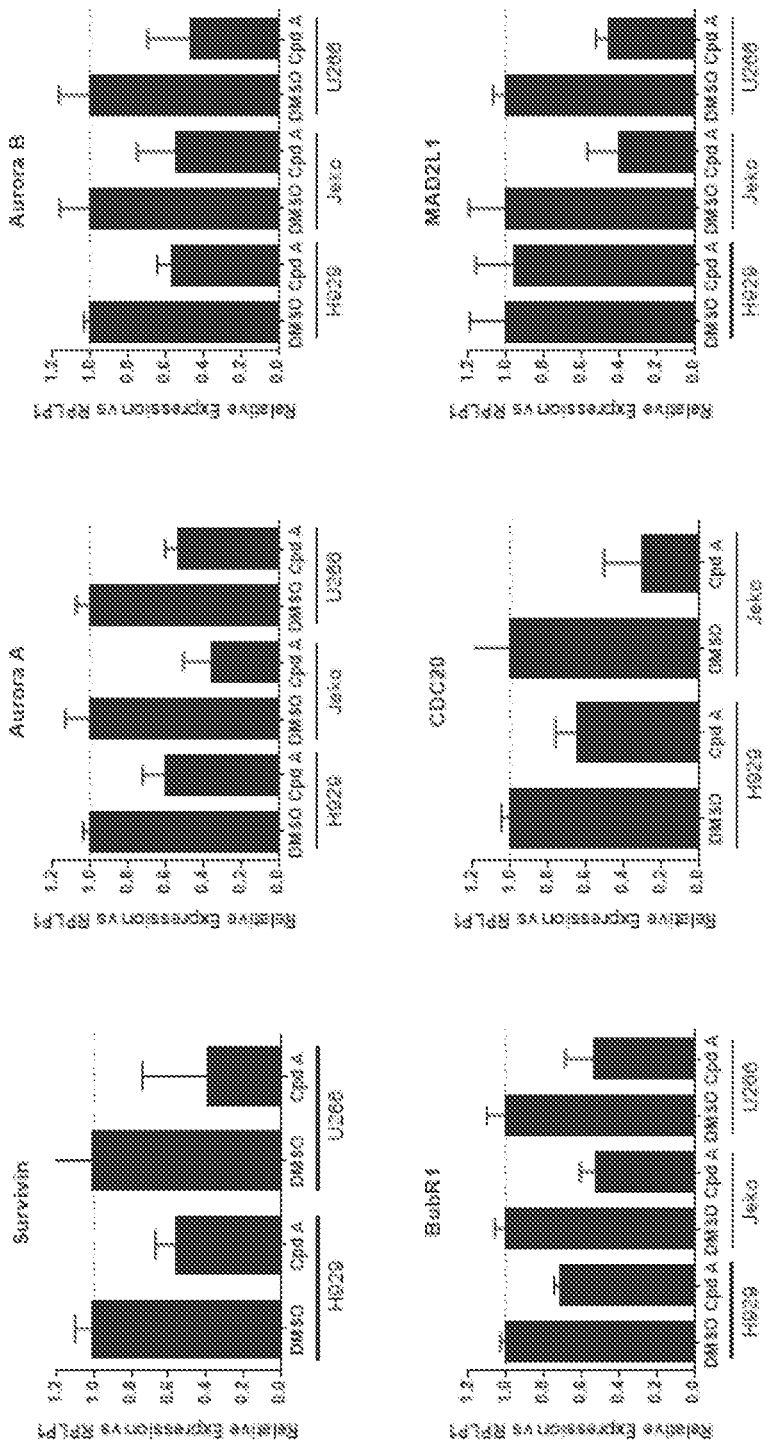
FIG. 2 is a series of bar graphs showing relative gene expression (as compared to housekeeping gene RPLP1) in H929 multiple myeloma cells, U266 multiple myeloma cells and Jeko-1 mantle cell lymphoma cells treated with Compound A or with DMSO.

The cells were treated with Compound A. Total RNA was extracted and gene expression was measured by quantitative polymerase chain reaction (PCR) analysis. FIG. 2 shows the relative fold induction (as compared to the housekeeping gene Ribosomal Protein Lateral Stalk Subunit P1, indicated herein as RPLP1 gene) as compared to DMSO treated cells for each indicated gene transcript (i.e., survivin, Aurora A, Aurora B, BubR1, CDC20 and MAD2L1). Each of these genes is part of the spindle assembly checkpoint, and the data confirm that treatment with Compound A reduced the expression of these key mitotic regulatory genes in multiple cell lines from different tumor types.

Example 5

Figure 3:
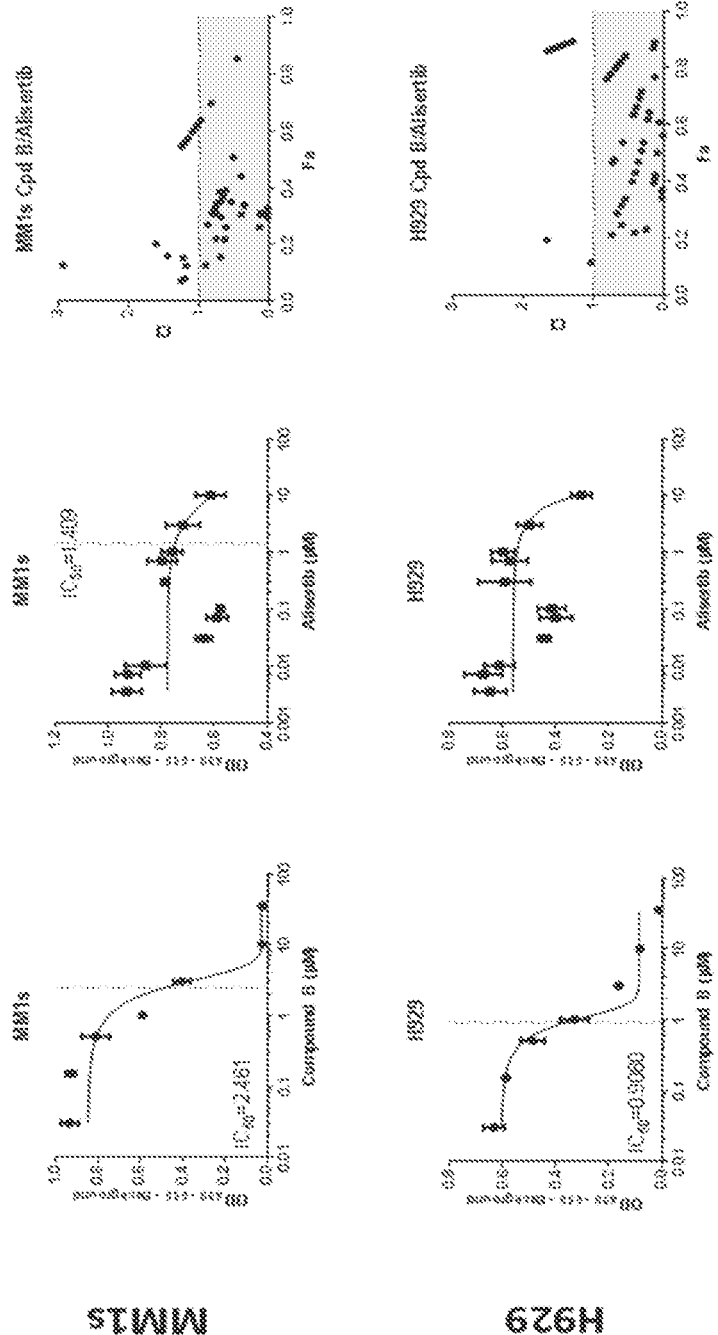
FIG. 3 is a series of graphs showing IC50 data, cell viability data and fraction affected combination index data for H929 cells and MM. 1s multiple myeloma cells treated with increasing doses of Compound B (left panels) or alisertib (middle panels) as single agents or in combination (right panels).

Combination of Compound B and Alisertib Synergistically Decrease Myeloma Cell Growth and Viability The combination of Compound B and alisertib was analyzed to determine whether the combination decreases myeloma cell growth and viability. H929 MM cells and MM1s myeloma cells were seeded in 384-well plates and treated in quadruplicate in a dose-matrix format with increasing doses of Compound B or alisertib as single agents or in combination. The cells were incubated for 48 hours. Total cell viability was assessed using an Aqueous One MTS assay (Promega Inc.; Fitchburg, WI). The fraction affected (Fa) was subsequently determined for each dose combination and the combination index (CI) was assessed using the Chou-Talalay method. For FIG. 3, the CI values less than one represent a synergistic effect, values equal to one suggest an additive effect, and values greater than two indicate an antagonistic effect. As shown in FIG. 3 (right panels), treatment of the myeloma cells with both Compound B and alisertib resulted in synergistic suppression of viability in both myeloma cell lines across a broad range of Fa values. This is evidenced by the large number of data points (representing individual dose combinations) in the Fa-CI plot that fall below the synergy cutoff of 1.0.

Example 6

Figure 4:
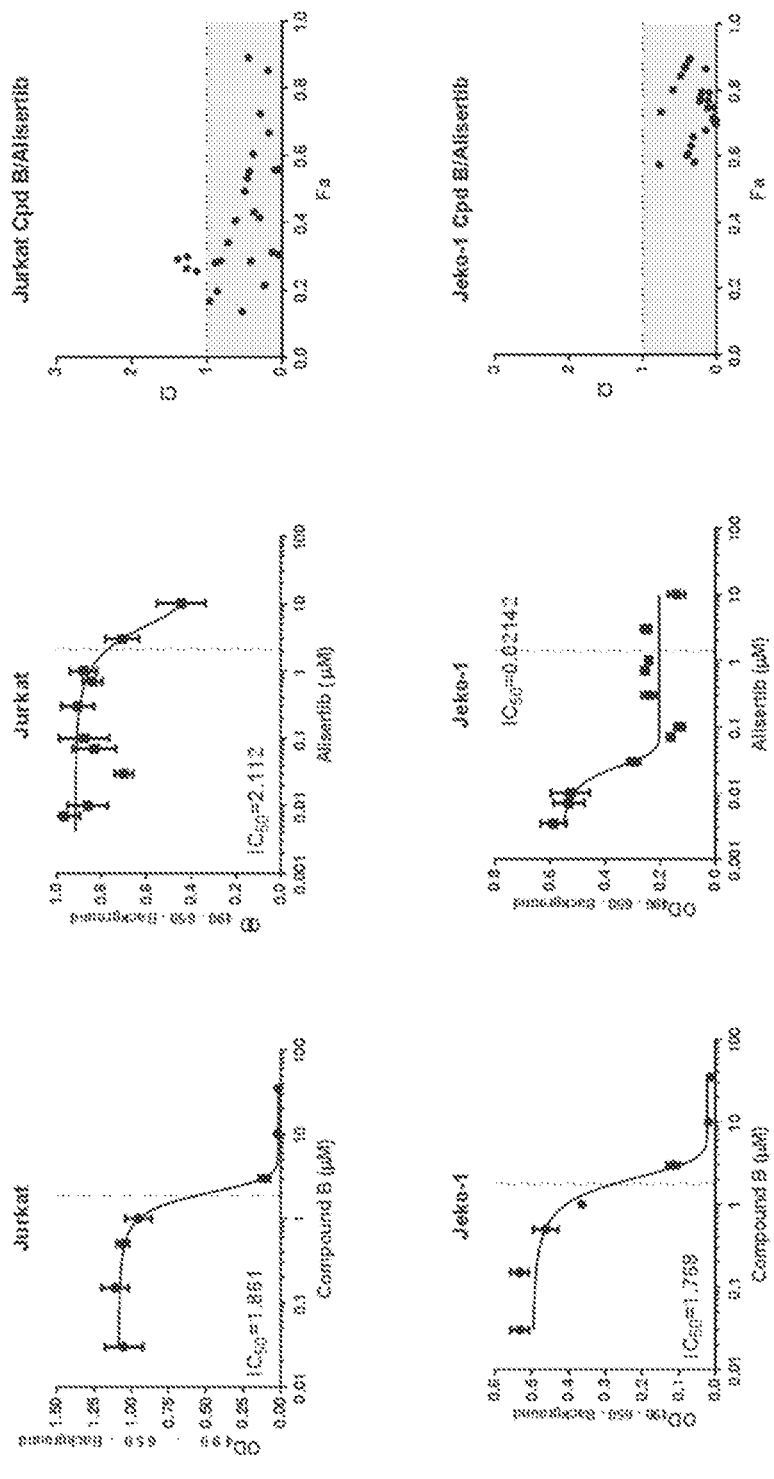
FIG. 4 is a series of graphs showing IC50 data, cell viability data and fraction affected combination index data for Jurkat T cells or Jeko-1 mantle cell lymphoma cells treated with increasing doses of Compound B (left panels) or alisertib (middle panels) as single agents or in combination (right panels).

Combination of Compound B and Alisertib Synergistically Decrease Lymphoma Cell Growth and Viability The combination of Compound B and alisertib results in synergistic decreases in lymphoma cell growth and viability. Jurkat T cell lymphoma or Jeko-1 mantle cell lymphoma cells were seeded in 384-well plates and treated in quadruplicate in a dose-matrix format with increasing doses of Compound B, alisertib or combinations of Compound B and alisertib (FIG. 4). The cells were incubated for 48 hours, and total cell viability was assessed via an MTS assay (Aqueous One, Promega Inc.). The fraction affected (Fa) was subsequently determined for each dose combination and the combination index (CI) was assessed using the method of Chou-Talalay. As evidenced in the Fa-CI plots in the right panels of FIG. 4, treatment of the cells of both lymphoma cell lines with Compound B and alisertib resulted in synergistic decrease in cell growth and viability across a broad range of Fa values. This is evidenced by the large number of data points (representing individual dose combinations) in the Fa-CI plot that fall below the synergy cutoff of 1.0.

Example 7

Administration of Both Compound B and Alisertib Increases Apoptosis

Figure 5:
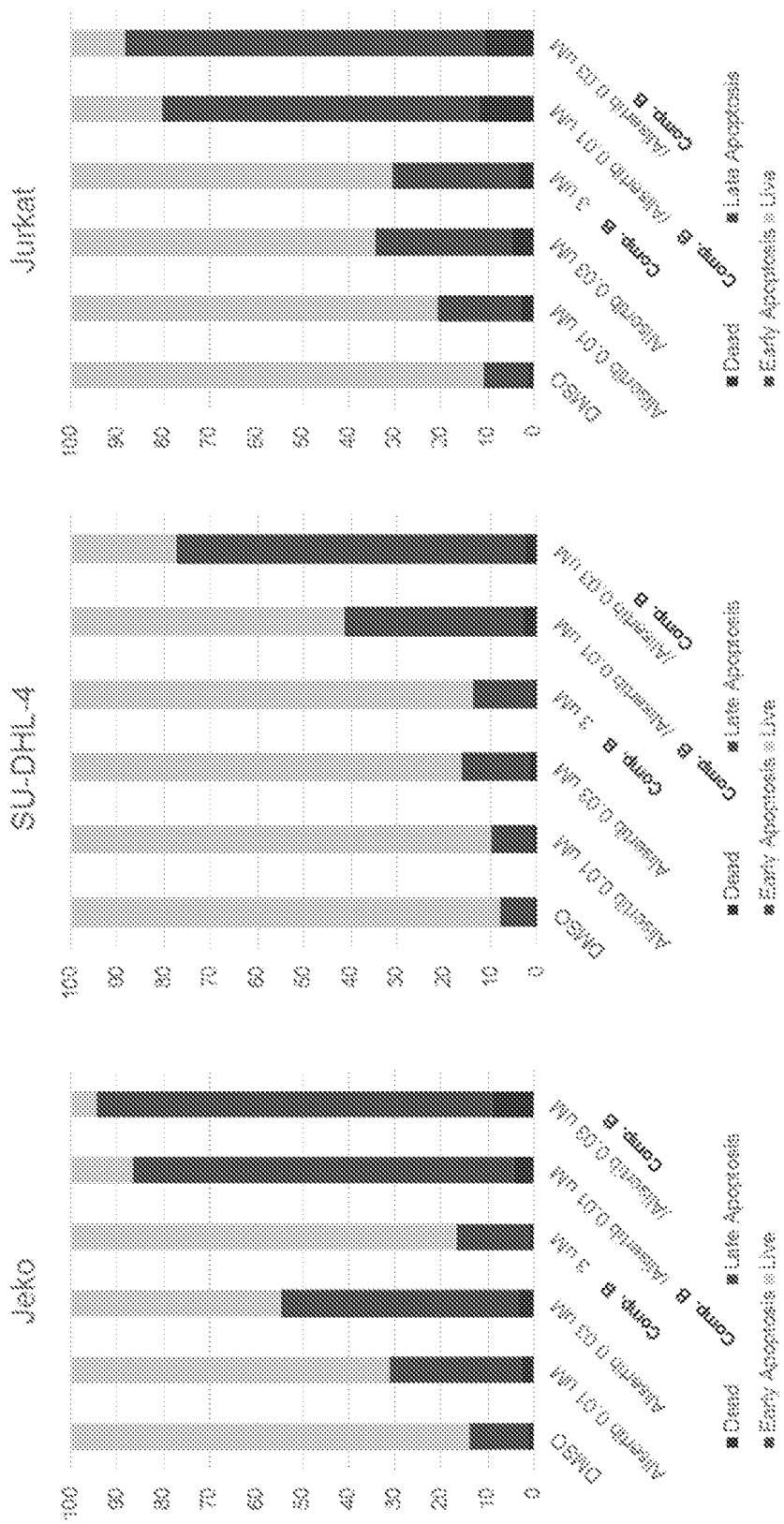
FIG. 5 is a series of graphs showing cell viability and apoptosis analysis of Jeko-1 mantle cell lymphoma cells, SU-DHL-4 B cell lymphoma cells, and Jurkat T cell lymphoma cells that were treated for 72 hours with either DMSO, 3 µM Compound B, 0.01 µM or 0.03 µM alisertib, or the combination of both drugs. Cells were characterized as either dead, late apoptotic, early apoptotic, or live.

To test for induction of apoptosis, Jeko-1 mantle cell lymphoma, SU-DHL-4 B cell lymphoma, and Jurkat T cell lymphoma cells were treated for 72 hours with either: DMSO, 3 µM of Compound B, 0.01 µM of alisertib, 0.03 µM of alisertib, or a combination of both Compound B and alisertib for 72 hrs. Cells were then harvested and stained with Annexin V, which recognizes an epitope on cells in the early stages of apoptosis. Cells were also stained with propidium iodide, which is excluded from cells with intact membranes, thus marking only dead cells. Flow cytometry analysis was then performed to measure the number of healthy and apoptotic cells under each treatment condition. In some cell lines, treatment with low doses of each compound individually resulted in some induction of apoptosis. Most importantly, combination treatment with Compound B and alisertib greatly increased the percentage of cells undergoing apoptosis relative to either single agent (FIG. 5).

Example 8

Figure 6:
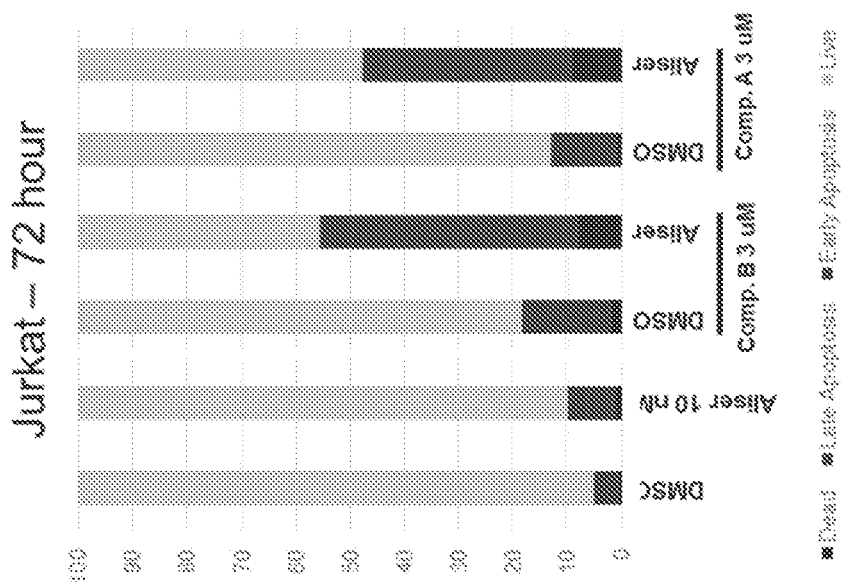
FIG. 6 is a graph showing cell viability and apoptosis analysis of Jurkat T cell lymphoma cells that were treated for 72 hours with either DMSO, 3 µM Compound B, 3 µM Compound A, 0.01 µM alisertib, or the combination of either HDAC inhibitor (i.e., Compound B or Compound A) with alisertib.

Administration of Compound A/Alisertib and Compound B/Alisertib Combinations Increases Apoptosis To determine the extent that the combination therapies of Compound A/alisertib and Compound B/alisertib promote induction of apoptosis, Jurkat T cell lymphoma cells were treated with: DMSO, 3 µM of Compound B, 3 µM of Compound A, 0.01 µM of alisertib, a combination of Compound B/alisertib, or a combination of Compound A/alisertib, for 72 hours. Cells were then harvested and stained with Annexin V and propidium iodide as above. Flow cytometry analysis was then used to measure the number of healthy and apoptotic cells under each treatment condition. While treatment with low doses of each compound individually resulted in minimal induction of apoptosis, combination treatment with alisertib plus either Compound A or Compound B greatly increased the percentage of cells undergoing apoptosis (FIG. 6).

Example 9

Administration of Both Compound B and Alisertib Increases Aneuploidy Frequency

Figure 7:
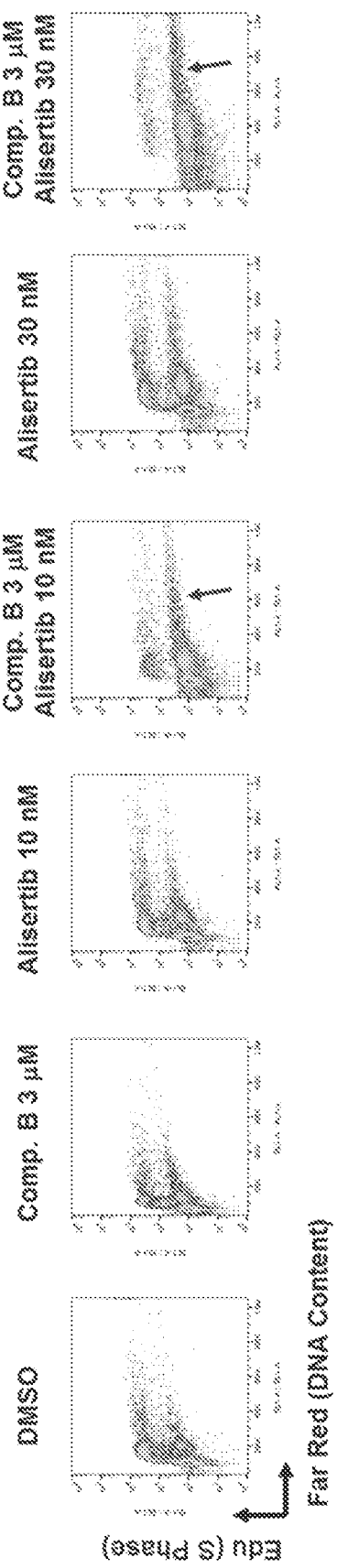
FIG. 7 is a series of flow cytometry dot plots showing relative DNA content for Jurkat T cell lymphoma cells that were treated for 48 hours with DMSO, 3 µM Compound B, 0.01 µM or 0.03 µM alisertib, or the combination of both drugs. The frequency of cells with abnormally high DNA content (i.e., >2n chromosomes) was found to dramatically increase upon combination treatment (see arrows).

To test the effects of combination treatment on DNA content, Jurkat T cell lymphoma cells were treated for 48 hours with either DMSO, 3 µM of Compound B, 0.01 µM of alisertib, 0.03 µM of alisertib, or the combination of Compound B and alisertib. DNA replication was assessed using 5-ethynyl-2'-deoxyuridine (EdU) label. Edu is a nucleotide analog of thymidine and is incorporated into DNA during active DNA synthesis. Total DNA content was determined using a Fx FarCycle Red stain. DNA replication and content were then measured using flow cytometry techniques. The frequency of cells with abnormally high DNA content (i.e., >2n) was found to dramatically increase upon combination treatment (indicated by arrows in FIG. 7); the data indicate that combination treatment was disrupting mitosis to result in cells with abnormal DNA content (FIG. 7), consistent with the downregulation of mitotic regulatory genes described above.

Those skilled in the art will recognize, or be able to ascertain using no more than routine experimentation, many equivalents of the specific embodiments of the invention described herein. Such equivalents are intended to be encompassed by the following claims.

The invention claimed is:

1. A pharmaceutical combination comprising a histone deacetylase 6 (HDAC6) inhibitor and an aurora kinase inhibitor, wherein the HDAC6 inhibitor is

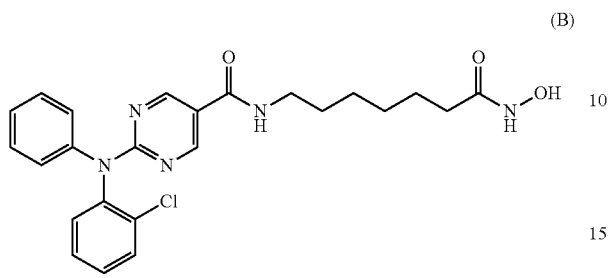

(B)

or a pharmaceutically acceptable salt thereof and the aurora kinase inhibitor is alisertib, or a pharmaceutically acceptable salt thereof.

2. The pharmaceutical combination of claim 1, wherein the HDAC6 inhibitor and the aurora kinase inhibitor are in the same formulation.

3. The pharmaceutical combination of claim 1, wherein the HDAC6 inhibitor and the aurora kinase inhibitor are in separate formulations.

4. The pharmaceutical combination of claim 1, wherein the combination is for simultaneous or sequential administration.

* * * * *